(12) United States Patent
Nakatsugawa et al.

(10) Patent No.: US 9,592,017 B2
(45) Date of Patent: Mar. 14, 2017

(54) RADIOGRAPHIC IMAGING DEVICE AND COMPUTER READABLE MEDIUM

(71) Applicant: FUJIFILM CORPORATION, Minato-ku, Tokyo (JP)

(72) Inventors: Haruyasu Nakatsugawa, Kanagawa (JP); Yasunori Ohta, Kanagawa (JP); Naoyuki Nishino, Kanagawa (JP); Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 14/700,166

(22) Filed: Apr. 30, 2015

(65) Prior Publication Data
US 2015/0245805 A1    Sep. 3, 2015

Related U.S. Application Data

(63) Continuation of application No. 13/859,763, filed on Apr. 10, 2013, now Pat. No. 9,050,051, which is a
(Continued)

(30) Foreign Application Priority Data

Oct. 26, 2010  (JP) ................................. 2010-240076

(51) Int. Cl.
*A61B 6/00* (2006.01)
*G01T 1/24* (2006.01)
(Continued)

(52) U.S. Cl.
CPC .......... *A61B 6/4233* (2013.01); *A61B 6/5205* (2013.01); *A61B 6/548* (2013.01);
(Continued)

(58) Field of Classification Search
CPC ....... A61B 6/4233; A61B 6/4283; A61B 6/54; A61B 6/542; G01N 23/40; G01T 1/16; G01T 1/17; G01T 1/247
See application file for complete search history.

(56) References Cited

U.S. PATENT DOCUMENTS

| 9,050,051 B2 * | 6/2015 | Nakatsugawa ...... A61B 6/4233 |
| 2004/0096035 A1 | 5/2004 | Yamazaki et al. |
| 2014/0061496 A1 | 3/2014 | Nakatsugawa |

FOREIGN PATENT DOCUMENTS

| JP | 51-140588 A | 12/1976 |
| JP | 07-201490 A | 8/1995 |

(Continued)

OTHER PUBLICATIONS

Written Opinion of the ISA issued in International Application No. PCT/JP2011/073577 mailed on Dec. 20, 2011.
(Continued)

*Primary Examiner* — Mark R Gaworecki
(74) *Attorney, Agent, or Firm* — SOLARIS Intellectual Property Group, PLLC

(57) ABSTRACT

The radiographic imaging device including: a radiation detector comprising plural radiographic image acquisition pixels, which are arranged in a matrix in an imaging region, for capturing a radiographic image and that acquire image information representing the radiographic image by converting applied radiation into electric charges and storing the electric charges, and a plural radiation detection pixels that detect the applied radiation by converting the applied radiation into electric charges and storing the electric charges, a subset of the plural radiation detection pixels having different characteristics; and a detecting unit that uses the radiation detection pixels selectively according to the different characteristics to detect a state of application of the radiation.

13 Claims, 16 Drawing Sheets

Related U.S. Application Data continuation of application No. PCT/JP2011/073577, filed on Oct. 13, 2011.

(51) Int. Cl.
 *H04N 5/32* (2006.01)
 *G01T 1/17* (2006.01)
 *G03B 42/04* (2006.01)

(52) U.S. Cl.
 CPC .................. *G01T 1/17* (2013.01); *G01T 1/24* (2013.01); *G03B 42/04* (2013.01); *H04N 5/32* (2013.01); *A61B 6/4283* (2013.01); *A61B 6/542* (2013.01); *A61B 6/563* (2013.01)

(56) References Cited

FOREIGN PATENT DOCUMENTS

| JP | 11-188021 A | 7/1999 |
| JP | 2001-305232 A | 10/2001 |
| JP | 2004-166724 | 6/2004 |
| JP | 2004-170216 A | 6/2004 |
| JP | 2004-223157 A | 8/2004 |
| JP | 2005-211514 A | 8/2005 |
| JP | 2008-264519 | 11/2008 |

OTHER PUBLICATIONS

International Search Report issued in International Application No. PCT/JP2011/073577 mailed on Dec. 20, 2011.

Japanese Office action dated Jul. 29, 2014 from the Japanese Patent Office in a Japanese patent application No. 2012-540767.

* cited by examiner

INITIAL INFORMATION INPUT SCREEN

PLEASE INPUT NAME OF SUBJECT, PART TO BE IMAGED, POSTURE IN WHICH IMAGING IS TO BE PERFORMED, AND EXPOSURE CONDITIONS.

NAME

PART TO BE IMAGED

POSTURE IN WHICH IMAGING IS TO BE PERFORMED

EXPOSURE CONDITIONS
- TUBE VOLTAGE
- TUBE CURRENT

END

RADIOGRAPHIC IMAGING DEVICE AND COMPUTER READABLE MEDIUM

CROSS-REFERENCE TO RELATED APPLICATIONS

This application is a continuation application of U.S. application Ser. No. 13/859,763, filed Apr. 10, 2013, which is a continuation of International Application No. PCT/2011/073577, filed Oct. 13, 2011. Further, this application claims priority from Japanese Patent Application No. 2010-240076, filed Oct. 26, 2010. The entire disclosure of each of the above-referenced applications is hereby incorporated by reference.

BACKGROUND OF THE INVENTION

Technical Field

The present invention pertains to a radiographic imaging device and a computer readable medium storing a program, and particularly relates to a radiographic imaging device that captures a radiographic image represented by radiation that has passed through a part to be imaged and to a computer readable medium storing a program executed by the radiographic imaging device.

Background Art

In recent years, radiation detectors such as flat panel detectors (FPD), in which a radiation-sensitive layer is placed on a thin-film transistor (TFT) active matrix substrate and which can directly convert radiation into digital data, have been put into practical use, and radiographic imaging devices that use these radiation detectors to capture radiographic images expressed by applied radiation have also been put into practical use. There are different methods by which the radiation detectors used in these radiographic imaging devices convert the radiation, and these include the indirect conversion method, in which the radiation is converted into light by a scintillator and thereafter the light is converted into electric charges by a semiconductor layer of photodiodes or the like, and the direct conversion method, in which the radiation is converted into electric charges by a semiconductor layer of amorphous selenium or the like, and in each method, there exist various materials that can be used for the semiconductor layer.

Incidentally, in this type of radiographic imaging device, if the start of the application of the radiation, the stopping of the application of the radiation, and the applied dose of the radiation can be detected by the radiographic imaging device itself, it becomes unnecessary to connect the radiographic imaging device to the radiation source and the imaging controller that collectively controls the radiographic imaging device and the radiation source, so this is preferred for simplifying the system configuration and simplifying the control by the imaging controller.

As a technology relating to this kind of radiographic imaging device that can detect the state of application of the radiation, in JP-A No. H07-201490, there is disclosed an X-ray diagnostic system includes an X-ray-to-optical signal converting unit that converts X-rays into optical signals, optical-to-electrical signal converting means that captures, with plural pixels, the optical signals converted by the X-ray-to-optical signal converting means and converts the optical signals into electrical signals, and X-ray exposure dose controlling means that controls the X-ray exposure dose with the electrical signal values of some of the pixels of the optical-to-electrical converting means.

Further, in JP-A No. 2005-223157, there is disclosed a radiographic imaging device having a radiographic image detector that detects a radiographic image of a subject, plural radiation dose detectors that detect the dose of radiation from the subject, and a controller that determines the mode of utilizing the outputs of the plural radiation dose detectors on the basis of the placement of the radiographic imaging device.

Moreover, in JP-A No. 2004-170216, there is disclosed a radiation detector having a radiation converter in which conversion elements that convert incident radiation into electrical signals are disposed on a substrate, wherein the radiation converter has first pixels, in which the conversion elements are connected to signal lines via switch elements that transfer the electrical signals and which output signals for generating an image, and second pixels, in which the conversion elements are directly connected to the signal lines and which detect the application of the radiation.

SUMMARY OF INVENTION

However, in the technologies disclosed in JP-A No. H07-201490, JP-A No. 2004-223157, and JP-A No. 2004-170216, although the state of application of the radiation can be detected by the devices themselves, depending on the imaging conditions for capturing the radiographic image, it is not always the case that the state of application of the radiation can be suitably detected.

That is, for example, in the case of capturing a radiographic image using only part of an imaging region resulting from the radiographic imaging device, such as when the part to be imaged is a leg, an arm, or the like, ordinarily imaging is performed with the part to be imaged being positioned in the central portion of the imaging region. For this reason, the levels of radiation doses that are detected differ greatly between the radiation dose obtained by radiation detection pixels disposed in the imaging region where the part to be imaged is not positioned and the radiation dose obtained by radiation detection pixels disposed in the imaging region where the part to be imaged is positioned, so in a case where the characteristics of each of the radiation detection pixels are fixed in common, there are cases where the radiation dose of one ends up becoming saturated and the signal-to-noise ratio (S/N ratio) of the radiation dose of the other ends up being remarkably low.

Further, for example, in the case of capturing a moving radiographic image, the radiation dose is reduced compared to the case of capturing a still radiographic image, but even in a case where the characteristics of the radiation detection pixels are fixed in common between capturing a moving image and capturing a still image, there are cases where the radiation dose of one ends up becoming saturated and the signal-to-noise ratio (S/N ratio) of the radiation dose of the other ends up being remarkably low.

The present invention provides a radiographic imaging device and a computer readable medium storing a program that can detect a state of application of radiation more accurately.

According to a first aspect of the present invention, there is provided a radiographic imaging device including: a radiation detector including plural radiographic image acquisition pixels that are arranged in a matrix in an imaging region for capturing a radiographic image and that acquire image information representing the radiographic image by converting applied radiation into electric charges and storing the electric charges, and plural radiation detection pixels arranged in an imaging region that detect the applied radiation by converting the applied radiation into electric charges and storing the electric charges, a subset of the plural radiation detection pixels having different characteristics; and a detecting unit that uses the radiation detection pixels selectively according to the different characteristics to detect a state of application of the radiation.

According to the radiographic imaging device according to the first aspect, the image information representing the radiographic image is acquired by the radiation detector as a result of the applied radiation being converted into electric charges and the electric charges being stored by the plural radiographic image acquisition pixels arranged in a matrix in the imaging region for capturing the radiographic image.

Here, in the present invention, a subset of the plural radiation detection pixels have different characteristics, and detect the applied radiation by converting the applied radiation into electric charges and storing the electric charges are used selectively according to the different characteristics and the state of application of the radiation is detected by the detecting unit.

In this way, according to the radiographic imaging device according to the first aspect, the subset of the plural radiation detection pixels that have different characteristics are arranged in the radiation detector, and the radiation detection pixels are used selectively according to the different characteristics to detect the state of application of the radiation, therefore the state of application of the radiation can be detected more accurately compared to a case where the radiation detector does not have these pixels.

According to a second aspect of the present invention, in the first aspect, the radiographic imaging device may further include an acquiring unit that acquires an imaging condition for capturing the radiographic image, and the detecting unit may use the radiation detection pixels which have characteristics corresponding to the imaging condition acquired by the acquiring unit to detect the state of application of the radiation. Because of this, the state of application of the radiation can be detected more accurately compared to a case where the pixels are selected independently of the imaging condition.

Further, according to a third aspect of the present invention, in the first or second aspect, the radiation detection pixels may be arranged in different positions in the imaging region. Because of this, the state of application of the radiation can be detected more accurately as a result of being able to select and use, in accordance with the size and so forth of the part to be imaged, the pixels used to detect the state of application of the radiation.

Further, according to a fourth aspect of the present invention, in any of the first to third aspects, the state of application of the radiation may be at least one of a start of application of the radiation, an end of application of the radiation, or an applied dose of the radiation, and the detecting unit may select the radiation detection pixels used in the detection of the state of application in accordance with the state of application of the radiation to be detected. Because of this, the state of application of the radiation can be detected more accurately as a result of being able to select and use, in accordance with the state of application of the radiation to be detected, the pixels used to detect the state of application.

Further, according to a fifth aspect of the present invention, in any of the first to fourth aspects, the subset of radiation detection pixels have different characteristics due to being connected to amplifiers that amplify, at different gains, signals represented by the electric charges stored by the subset of radiation detection pixels. According to a sixth aspect of the present invention, in any of the first to fifth aspects, the subset of radiation detection pixels have different characteristic due to being connected to low-pass filters that perform low-pass filtering at different low-pass filtering frequencies with respect to signals represented by the electric charges stored by the subset of radiation detection pixels. According to a seventh aspect of the present invention, in any of the first to sixth aspects, the subset of radiation detection pixels have different characteristics due to being connected to a synthesizing unit that synthesize different numbers of signals represented by the electric charges stored by the subset of radiation detection pixels. Because of this, the characteristics of the pixels that have different characteristics can be realized easily.

Further, according to an eighth aspect of the present invention, in the second aspect, the imaging condition is at least one of a part to be imaged, a region in which the part to be imaged is placed when capturing the radiographic image, whether the imaging is imaging to capture a moving image or a still image, or an applied dose of the radiation. Because of this, the state of application of the radiation can be detected more accurately in accordance with the applied imaging condition.

Moreover, according to a ninth aspect of the present invention, in any of the first to eighth aspects, the radiation detector may be further includes dedicated lines for reading out the stored electric charges from the radiation detection pixels. Because of this, the radiographic image can be captured at a higher speed as a result of being able to detect the state of application of the radiation independently of the action of capturing the radiographic image.

According to a tenth aspect of the present invention, there is provided a computer readable medium storing a program executed by a radiographic imaging device including a radiation detector that includes plural radiographic image acquisition pixels that are arranged in a matrix in an imaging region for capturing a radiographic image and that acquire image information representing the radiographic image by converting applied radiation into electric charges and storing the electric charges and plural radiation detection pixels that are arranged in the imaging region, and that detect the applied radiation by converting the applied radiation into electric charges and storing the electric charges, a subset of the plural radiation detection pixels having different characteristics, the program causing a computer to function as an acquiring unit that acquires an imaging condition for capturing the radiographic image and a detecting unit that uses the radiation detection pixels having characteristics corresponding to the imaging condition acquired by the acquiring unit to detect a state of application of the radiation.

Consequently, according to the invention according to the tenth aspect, a computer can be caused to act in the same way as the radiographic imaging device of the present invention, therefore, like the radiographic imaging device the state of application of the radiation can be detected more accurately.

According to the present invention, the subset of radiation detection pixels that have different characteristics are arranged in the radiation detector, and these pixels are used selectively according to the characteristics to detect the state of application of the radiation, therefore the state of application of the radiation can be detected more accurately compared to a case where the radiation detector does not have these pixels.

BRIEF DESCRIPTION OF DRAWINGS

FIG. 12 is a schematic diagram showing an example of an initial information input screen pertaining to the embodiment;

DETAILED DESCRIPTION OF THE INVENTION

An embodiment of the present invention will be described in detail below with reference to the drawings. Here, an example configuration in a case in which the present invention is applied to a radiology information system, which is a system that collectively manages information handled in a radiology department in a hospital, will be described.

Figure 1:
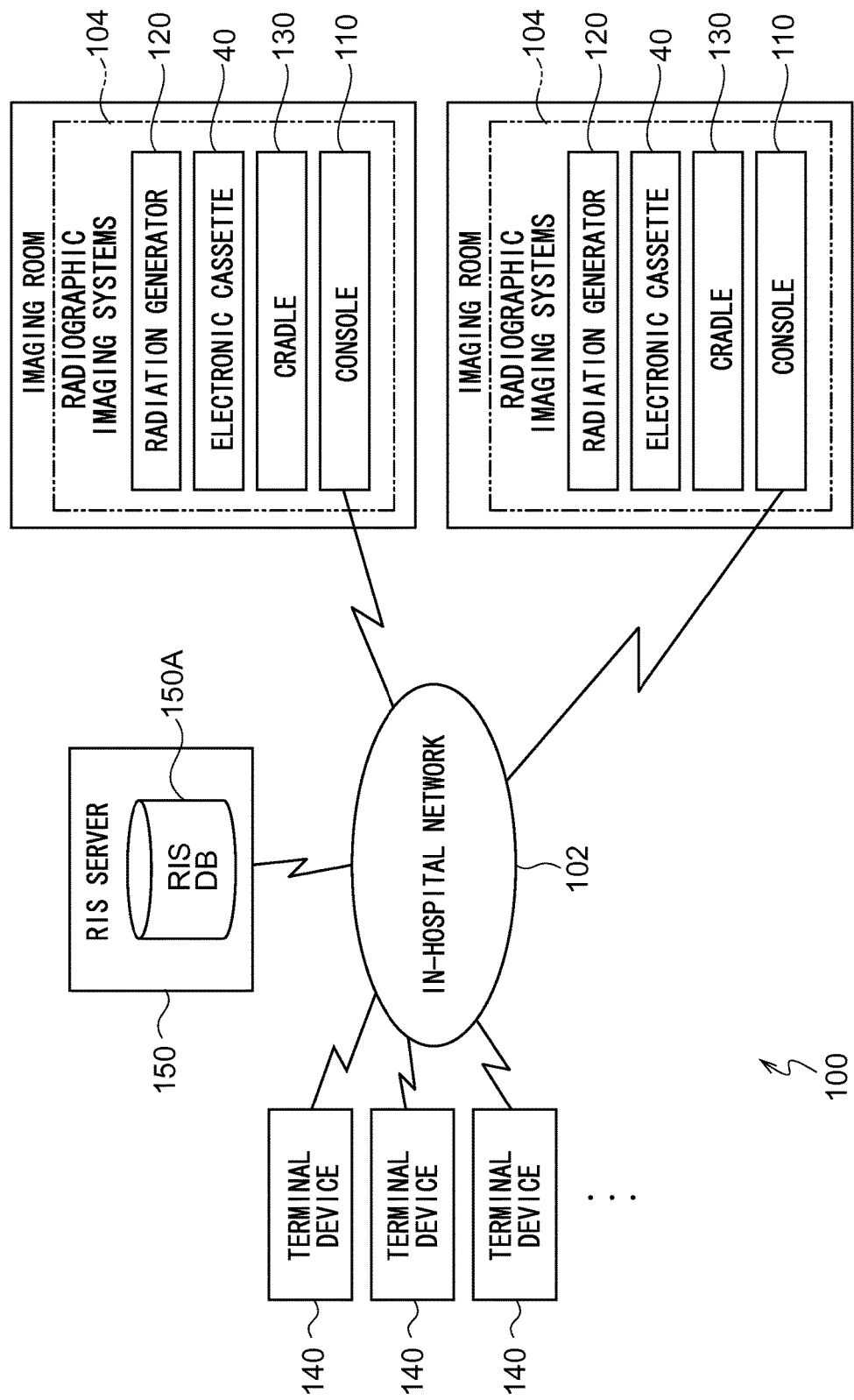
FIG. 1 is a block diagram showing the configuration of a radiology information system pertaining to an embodiment.

First, the configuration of a radiology information system (hereinafter called "RIS") 100 pertaining to the present embodiment will be described with reference to FIG. 1.

The RIS 100 is a system for managing information such as medical service appointments and diagnostic records in a radiology department and configures part of a hospital information system (hereinafter called "HIS").

The RIS 100 has plural imaging request terminal devices (hereinafter called "terminal devices") 140, an RIS server 150, and radiographic imaging systems (hereinafter called "imaging systems") 104 installed in individual radiographic imaging rooms (or operating rooms) in a hospital, and the RIS 100 is configured as a result of these being connected to an in-hospital network 102 including a wired or wireless local area network (LAN) or the like. The RIS 100 configures part of the HIS disposed in the same hospital, and an HIS server (not shown in the drawings) that manages the entire HIS is also connected to the in-hospital network 102.

The terminal devices 140 are for doctors or radiologic technologists to input and browse diagnostic information and facility reservations, and radiographic imaging requests and imaging reservations are also made via the terminal devices 140. Each terminal device 140 is configured to include a personal computer having a display device, and the terminal devices 140 are capable of intercommunication with the RIS server 150 via the in-hospital network 102.

The RIS server 150 receives the imaging requests from each of the terminal devices 140 and manages radiographic imaging schedules in the imaging systems 104, and the RIS server 150 is configured to include a database 150A.

The database 150A is configured to include: information relating to patients (subjects), such as attribute information (names, sexes, dates of birth, ages, blood types, body weights, patient identifications (IDs), etc.) of the patients, medical histories, consultation histories, radiographic images that have been captured in the past, etc.; information relating to later-described electronic cassettes 40 used in the imaging systems 104, such as identification numbers (ID information), models, sizes, sensitivities, dates of first use, numbers of times used, etc.; and environment information representing the environments in which the electronic cassettes 40 are used to capture radiographic images, that is, the environments in which the electronic cassettes 40 are used (e.g., radiographic imaging rooms, operating rooms, etc.).

The imaging systems 104 capture radiographic images as a result of being operated by the doctors or the radiologic technologists in response to an instruction from the RIS server 150. Each imaging system 104 includes: a radiation generator 120 that applies a dose of radiation X (see also FIG. 7) according to exposure conditions from a radiation source 121 (see also FIG. 2) to a subject; an electronic cassette 40 that has a built-in radiation detector 20 (see also FIG. 7) that absorbs the radiation X that has passed through the part of the subject to be imaged, generates electric charges, and creates image information representing a radiographic image on the basis of the generated electric charge quantity; a cradle 130 that charges a battery built into the electronic cassette 40; and a console 110 that controls the electronic cassette 40 and the radiation generator 120.

The console 110 acquires various types of information included in the database 150A from the RIS server 150, stores the information in a later-described HDD 116 (see FIG. 9), uses the information as needed, and controls the electronic cassette 40 and the radiation generator 120.

Figure 2:
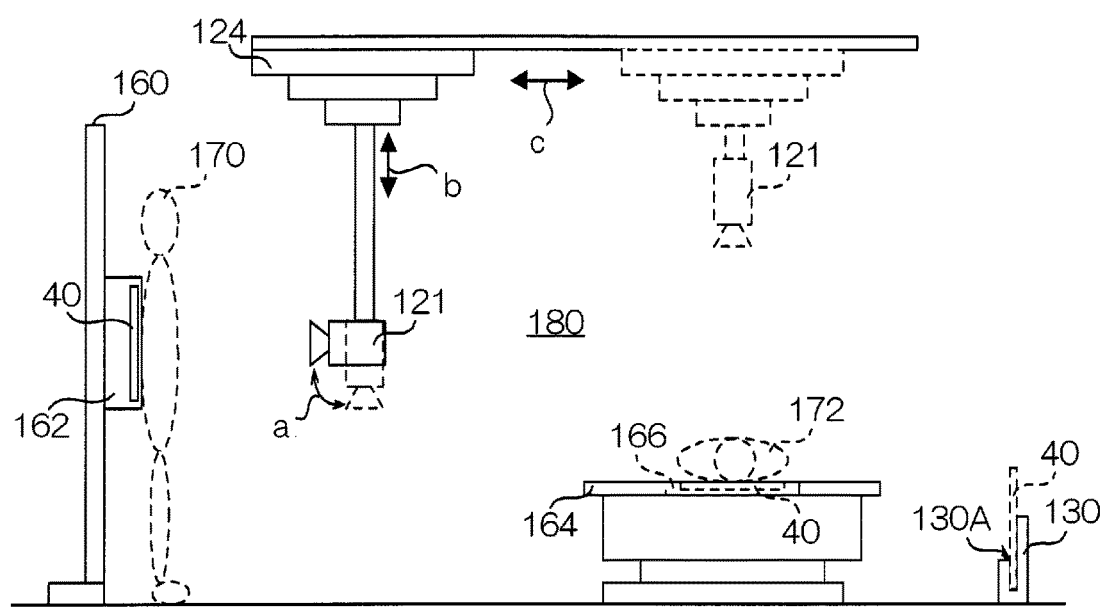
FIG. 2 is a side view showing an example of an arrangement of devices, in a radiographic imaging room, of a radiographic imaging system pertaining to the embodiment.

In FIG. 2, there is shown an example of an arrangement of the devices, in a radiographic imaging room 180, of the imaging system 104 pertaining to the present embodiment.

As shown in FIG. 2, an upright-position stand 160 used when performing radiographic imaging in an upright position and a recumbent-position table 164 used when performing radiographic imaging in a recumbent position are installed in the radiographic imaging room 180. The space in front of the upright-position stand 160 serves as a subject imaging position 170 when performing radiographic imaging in the upright position, and the space above the recumbent-position table 164 serves as a subject imaging position 172 when performing radiographic imaging in the recumbent position.

A holder 162 that holds the electronic cassette 40 is disposed in the upright-position stand 160, and the electronic cassette 40 is held in the holder 162 when capturing a radiographic image in the upright position. Likewise, a holder 166 that holds the electronic cassette 40 is disposed in the recumbent-position table 164, and the electronic cassette 40 is held in the holder 166 when capturing a radiographic image in the recumbent position.

Further, in order to enable both radiographic imaging in the upright position and radiographic imaging in the recumbent position with radiation from the single radiation source 121, a supporting and moving mechanism 124 that supports the radiation source 121 in such a way that the radiation source 121 is rotatable about a horizontal axis (the direction of arrow a in FIG. 2), is movable in the vertical direction (the direction of arrow b in FIG. 2), and is movable in the horizontal direction (the direction of arrow c in FIG. 2) is disposed in the radiographic imaging room 180. Here, the supporting and moving mechanism 124 includes a drive source that rotates the radiation source 121 about the horizontal axis, a drive source that moves the radiation source 121 in the vertical direction, and a drive source that moves the radiation source 121 in the horizontal direction (none of the drive sources are shown in the drawings).

An accommodating portion 130A capable of storing the electronic cassette 40 is formed in the cradle 130.

When the electronic cassette 40 is not in use, the built-in battery of the electronic cassette 40 is charged by the cradle 130 with the electronic cassette 40 stored in the accommodating portion 130A of the cradle 130, and when a radiographic image is to be captured, the electronic cassette 40 is removed from the cradle 130 by a radiologic technologist or the like and is held in the holder 162 of the upright-position stand 160 if the imaging posture is the upright position or is held in the holder 166 of the recumbent-position table 164 if the imaging posture is the recumbent position.

Here, in the imaging system 104 pertaining to the present embodiment, various types of information are transmitted and received by wireless communication between the radiation generator 120 and the console 110 and between the electronic cassette 40 and the console 110.

The electronic cassette 40 is not used only in a state in which it is held in the holder 162 of the upright-position stand 160 or the holder 166 of the recumbent-position table 164, but because it is portable, when imaging an arm, a leg, or the like, it can also be used in a state in which it is not held in the holders.

Figure 3:
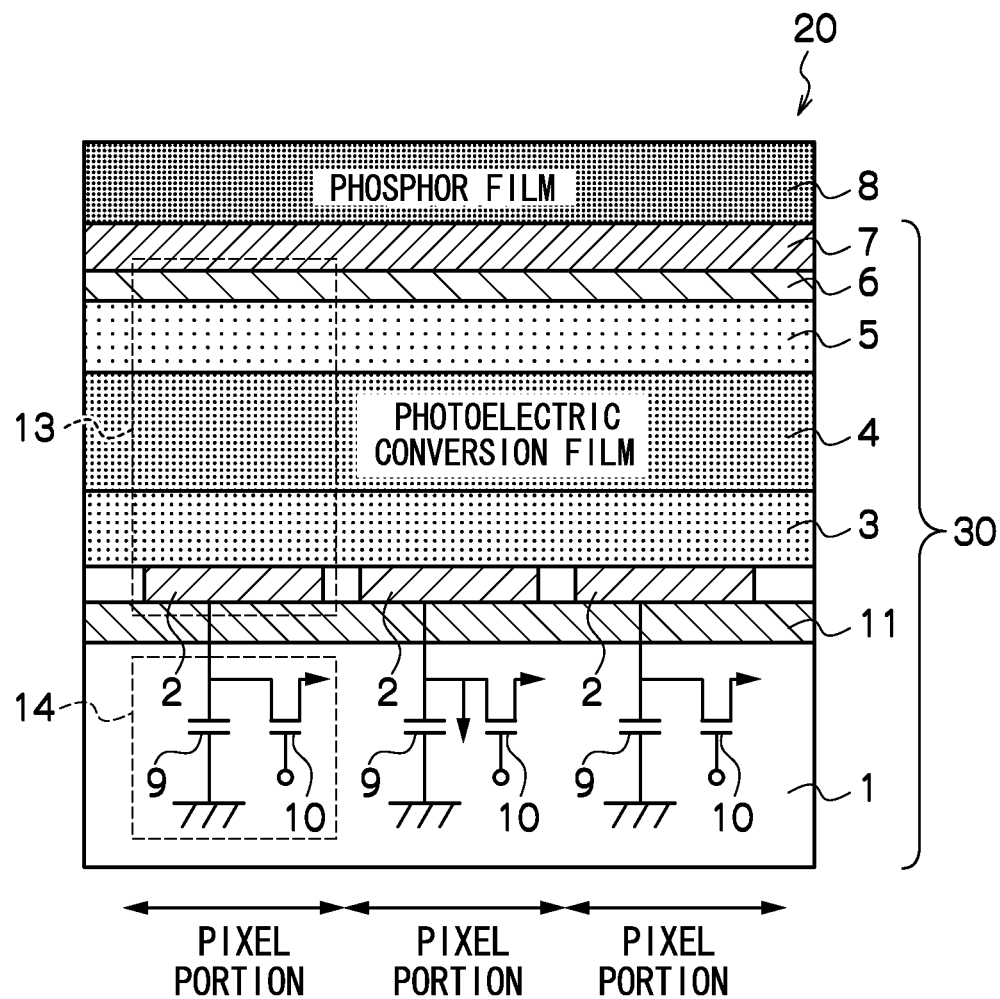
FIG. 3 is a cross-sectional schematic view showing the schematic configuration of three pixel sections of a radiation detector pertaining to the embodiment.

Next, the configuration of the radiation detector 20 pertaining to the present embodiment will be described. FIG. 3 is a cross-sectional schematic diagram schematically showing the configuration of three pixel sections of the radiation detector 20 pertaining to the present embodiment.

As shown in FIG. 3, in the radiation detector 20 pertaining to the present embodiment, signal output portions 14, sensor portions 13, and a scintillator 8 are sequentially layered on an insulating substrate 1, and pixels are configured by the signal output portions 14 and the sensor portions 13. The pixels are plurally arrayed on the substrate 1 and are configured in such a way that the signal output portion 14 and the sensor portion 13 in each pixel lie on top of one another.

The scintillator 8 is formed via a transparent insulating film 7 on the sensor portions 13 and includes a phosphor film that converts radiation made incident from above (the opposite side of the substrate 1 side) or below into light and luminesces. By disposing the scintillator 8, the scintillator 8 absorbs the radiation that has passed through the subject and luminesces.

It is preferred that the wavelength range of the light emitted by the scintillator 8 be in the visible light range (a wavelength of 360 nm to 830 nm), and it is more preferred that the wavelength range of the light emitted by the scintillator 8 include the green wavelength range in order to enable monochrome imaging by the radiation detector 20.

As the phosphor used for the scintillator 8, specifically a phosphor including cesium iodide (CsI) is preferred in the case of imaging using X-rays as the radiation, and using CsI(Tl) (cesium iodide to which thallium has been added) whose emission spectrum when X-rays are applied is 420 nm to 700 nm is particularly preferred. The emission peak wavelength, in the visible light range, of CsI(Tl) is 565 nm. The phosphor used for the scintillator is not limited to this, and GOS—and particularly GOS:Tb(Gd202S:Tb) (terbium-activated gadolinium oxysulfide)—or the like can also be used The emission peak wavelength, in the visible light range, of GOS:Tb is 550 nm.

The sensor portions 13 have an upper electrode 6, lower electrodes 2, and a photoelectric conversion film 4 that is placed between the upper and lower electrodes, and the photoelectric conversion film 4 is configured by an organic photoelectric conversion material that absorbs the light emitted by the scintillator 8 and generates an electric charge.

It is preferred that the upper electrode 6 be configured by a conducting material that is transparent at least with respect to the emission wavelength of the scintillator 8 because it is necessary to allow the light produced by the scintillator 8 to be made incident on the photoelectric conversion film 4; specifically, using a transparent conducting oxide (TCO) whose transmittance with respect to visible light is high and whose resistance value is small is preferred. A metal thin film of Au or the like can also be used as the upper electrode 6, but its resistance value tends to increase when trying to obtain a transmittance of 90% or more, so TCO is more preferred. For example, ITO, IZO, AZO, FTO, $SnO_2$, $TiO_2$, $ZnO_2$, and so forth can be preferably used, and ITO is most preferred from the standpoints of process ease, low resistance, and transparency. The upper electrode 6 may have a single-layer configuration common to all the pixels or may be divided per pixel.

The photoelectric conversion film 4 includes the organic photoelectric conversion material, absorbs the light emitted from the scintillator 8, and generates an electric charge corresponding to the absorbed light. The photoelectric conversion film 4 including the organic photoelectric conversion material in this way has a sharp absorption spectrum in the visible range, virtually no electromagnetic waves other than the light emitted by the scintillator 8 are absorbed by the photoelectric conversion film 4, and noise that is generated as a result of radiation such as X-rays being absorbed by the photoelectric conversion film 4 can be effectively suppressed.

It is preferred that the absorption peak wavelength of the organic photoelectric conversion material configuring the photoelectric conversion film 4 be as close as possible to the emission peak wavelength of the scintillator 8 so that the organic photoelectric conversion material most efficiently absorbs the light emitted by the scintillator 8. It is ideal that the absorption peak wavelength of the organic photoelectric conversion material and the emission peak wavelength of the scintillator 8 coincide, but as long as the difference between both is small, the organic photoelectric conversion material can sufficiently absorb the light emitted from the scintillator 8. Specifically, it is preferred that the difference between the absorption peak wavelength of the organic photoelectric conversion material and the emission peak wavelength of the scintillator 8 with respect to radiation be within 10 nm, and it is more preferred that the difference be within 5 nm.

Examples of organic photoelectric conversion materials capable of satisfying this condition include quinacridone organic compounds and phthalocyanine organic compounds. For example, the absorption peak wavelength, in the visible range, of quinacridone is 560 nm, so if quinacridone is used as the organic photoelectric conversion material and CsI(Tl) is used as the material of the scintillator 8, it becomes possible to make the difference between the peak wavelengths within 5 nm and the amount of electric charge generated in the photoelectric conversion film 4 can be substantially maximized. Also in the case of using GOS:Tb as the material of the scintillator 8, it is possible to make the difference between the peak wavelengths with quinacridone as the organic photoelectric conversion material about 10 nm, and the amount of electric charge generated by the photoelectric conversion film 4 can be substantially maximized.

Next, the photoelectric conversion film 4 applicable to the radiation detector 20 pertaining to the present embodiment will be specifically described.

The electromagnetic wave absorption/photoelectric conversion site in the radiation detector 20 pertaining to the present embodiment can be configured by the pair of electrodes 2 and 6 and an organic layer that includes the organic photoelectric conversion film 4 sandwiched between the electrodes 2 and 6. More specifically, this organic layer can be formed by stacking or mixing together a site that absorbs electromagnetic waves, a photoelectric conversion site, an electron-transporting site, a hole-transporting site, an electron-blocking site, a hole-blocking site, a crystallization preventing site, electrodes, and an interlayer contact improving site.

It is preferred that the organic layer includes an organic p-type compound or an organic n-type compound.

Organic p-type semiconductors (compounds) are donor organic semiconductors (compounds) represented mainly by hole-transporting organic compounds, are organic compounds having the property that they easily donate electrons, and more specifically are organic compounds whose ionization potential is the smaller of the two when two organic materials are brought into contact with each other and used. Consequently, any organic compound is usable as the donor organic compound provided that it is an electron-donating organic compound.

Organic n-type semiconductors (compounds) are accepter organic semiconductors (compounds) represented mainly by electron-transporting organic compounds, are organic compounds having the property that they easily accept electrons, and more specifically are organic compounds whose electron affinity is the greater of the two when two organic compounds are brought into contact with each other and used. Consequently, any organic compound is usable as the accepter organic compound provided that it is an electron-accepting organic compound.

Materials applicable as the organic p-type semiconductor and the organic n-type semiconductor, and the configuration of the photoelectric conversion film 4, are described in detail in JP-A No. 2009-32854, so description will be omitted. The photoelectric conversion film 4 may also be formed so as to further include fullerenes or carbon nanotubes.

It is preferred that the film thickness of the photoelectric conversion film 4 be as large as possible in terms of absorbing the light from the scintillator 8, but if the film thickness of the photoelectric conversion film 4 becomes thicker than a certain extent, the strength of the electric field generated in the photoelectric conversion film 4 by the bias voltage applied from both ends of the photoelectric conversion film 4 drops and the electric charges become unable to be collected, so the film thickness is preferably from 30 nm to 300 nm, more preferably from 50 nm to 250 nm, and particularly preferably from 80 nm to 200 nm.

In the radiation detector 20 shown in FIG. 3, the photoelectric conversion film 4 has a single-layer configuration common to all the pixels, but the photoelectric conversion film 4 may also be divided per pixel.

The lower electrodes 2 are thin films divided per pixel. The lower electrodes 2 can be configured by a transparent or opaque conducting material, and aluminum, silver, and so forth can be suitably used.

The thickness of the lower electrodes 2 can be 30 nm to 300 nm, for example.

In the sensor portions 13, one from the electric charge (holes, electrons) generated in the photoelectric conversion film 4 can be moved to the upper electrode 6 and the other can be moved to the lower electrodes 2 as a result of a predetermined bias voltage being applied between the upper electrode 6 and the lower electrodes 2. In the radiation detector 20 of the present embodiment, a wire is connected to the upper electrode 6, and the bias voltage is applied to the upper electrode 6 via this wire. Further, the polarity of the bias voltage is decided in such a way that the electrons generated in the photoelectric conversion film 4 move to the upper electrode 6 and the holes move to the lower electrodes 2, but this polarity may also be the opposite.

It suffices for the sensor portions 13 configuring each of the pixels to include at least the lower electrodes 2, the photoelectric conversion film 4, and the upper electrode 6, but in order to suppress an increase in dark current, disposing at least either of an electron-blocking film 3 and a hole-blocking film 5 is preferred, and disposing both is more preferred.

The electron-blocking film 3 can be disposed between the lower electrodes 2 and the photoelectric conversion film 4 and can suppress electrons from being injected from the lower electrodes 2 into the photoelectric conversion film 4 and dark current from ending up increasing when the bias voltage has been applied between the lower electrodes 2 and the upper electrode 6.

Electron-donating organic materials can be used for the electron-blocking film 3.

It suffices for the material that is actually used for the electron-blocking film 3 to be selected in accordance with, for example, the material of the adjacent electrodes and the material of the adjacent photoelectric conversion film 4, and a material whose electron affinity (Ea) is greater by 1.3 eV or more than the work function (Wf) of the material of the adjacent electrodes and has an ionization potential (Ip) equal to or smaller than the ionization potential of the material of the adjacent photoelectric conversion film 4 is preferred. Materials applicable as the electron-donating organic material are described in detail in JP-A No. 2009-32854, so description will be omitted.

In order to allow the electron-blocking film 3 to reliably exhibit a dark current suppressing effect and to prevent a drop in the photoelectric conversion efficiency of the sensor portions 13, the thickness of the electron-blocking film 3 is preferably from 10 nm to 200 nm, more preferably from 30 nm to 150 nm, and particularly preferably from 50 nm to 100 nm.

The hole-blocking film 5 can be disposed between the photoelectric conversion film 4 and the upper electrode 6 and can suppress holes from being injected from the upper electrode 6 into the photoelectric conversion film 4 and dark current from ending up increasing when the bias voltage has been applied between the lower electrodes 2 and the upper electrode 6.

Electron-accepting organic materials can be used for the hole-blocking film 5.

In order to allow the hole-blocking film 5 to reliably exhibit a dark current suppressing effect and to prevent a drop in the photoelectric conversion efficiency of the sensor portions 13, the thickness of the hole-blocking film 5 is preferably from 10 nm to 200 nm, more preferably from 30 nm to 150 nm, and particularly preferably from 50 nm to 100 nm.

It suffices for the material that is actually used for the hole-blocking film 5 to be selected in accordance with, for example, the material of the adjacent electrode and the material of the adjacent photoelectric conversion film 4, and a material whose ionization potential (Ip) is greater by 1.3 eV or more than the work function (Wf) of the material of the adjacent electrode and has an electron affinity (Ea) equal to or greater than the electron affinity of the material of the adjacent photoelectric conversion film 4 is preferred. Materials applicable as the electron-accepting organic material are described in detail in JP-A No. 2009-32854, so description will be omitted.

In a case where the bias voltage is set in such a way that, from the electric charge generated in the photoelectric conversion film 4, the holes move to the upper electrode 6 and the electrons move to the lower electrode 2, the positions of the electron-blocking film 3 and the hole-blocking film 5 may be reversed. Further, the electron-blocking film 3 and the hole-blocking film 5 do not both have to be disposed; a certain degree of a dark current suppressing effect can be obtained as long as either is disposed.

Figure 4:
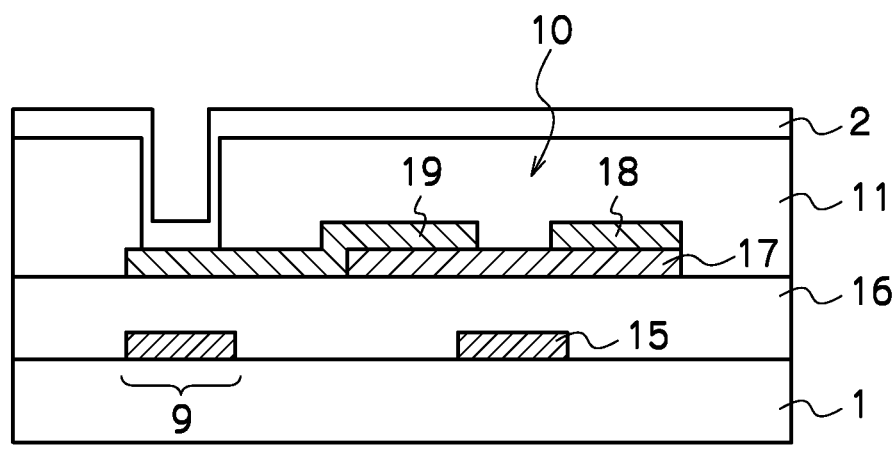
FIG. 4 is a cross-sectional side view schematically showing the configuration of a signal output portion of one pixel section of the radiation detector pertaining to the embodiment.

The signal output portions 14 are formed on the surface of the substrate 1 below the lower electrodes 2 of each of the pixels. In FIG. 4, the configuration of the signal output portions 14 is schematically shown.

As shown in FIG. 4, in each of the signal output portions 14 pertaining to the present embodiment, a capacitor 9 that stores the electric charge that has moved to the lower electrode 2 and a field-effect thin-film transistor (TFT) (hereinafter sometimes simply called a thin-film transistor) 10 that converts the electric charge stored in the capacitor 9 into an electrical signal and outputs the electrical signal are formed in correspondence to the lower electrode 2. The region in which the capacitor 9 and the thin-film transistor 10 are formed has a section that coincides with the lower electrode 2 as seen in a plan view, and by giving the signal output portion 14 this configuration, the signal output portion 14 and the sensor portion 13 lie on top of one another in the thickness direction. In order to minimize the plane area of the radiation detector 20 (the pixels), it is preferred that the region in which the capacitor 9 and the thin-film transistor 10 are formed be completely covered by the lower electrode 2.

The capacitor 9 is electrically connected to the corresponding lower electrode 2 via a wire of a conductive material that is formed penetrating an insulating film 11 disposed between the substrate 1 and the lower electrode 2.

Because of this, the electric charge trapped in the lower electrode 2 can be moved to the capacitor 9.

In the thin-film transistor 10, a gate electrode 15, a gate insulating film 16, and an active layer (channel layer) 17 are layered, and moreover, a source electrode 18 and a drain electrode 19 are formed a predetermined spacing apart from each other on the active layer 17.

The active layer 17 can, for example, be formed by amorphous silicon, an amorphous oxide, an organic semiconductor material, carbon nanotubes, or the like. The material configuring the active layer 17 is not limited to these.

As the amorphous oxide configuring the active layer 17, oxides including at least one of In, Ga, and Zn (e.g., In—O amorphous oxides) are preferred, oxides including at least two of In, Ga, and Zn (e.g., In—Zn—O amorphous oxides, In—Ga—O amorphous oxides, or Ga—Zn—O amorphous oxides) are more preferred, and oxides including In, Ga, and Zn are particularly preferred. As an In—Ga—Zn—O amorphous oxide, an amorphous oxide whose composition in a crystalline state is expressed by $InGaO_3(ZnO)_m$ (where m is a natural number less than 6) is preferred, and particularly $InGaZnO_4$ is more preferred.

Examples of organic semiconductor materials capable of configuring the active layer 17 include phthalocyanine compounds, pentacene, and vanadyl phthalocyanine, but the organic semiconductor materials are not limited to these. Configurations of phthalocyanine compounds are described in detail in JP-A No. 2009-212389, so description will be omitted.

By forming the active layer 17 of the thin-film transistor 10 from an amorphous oxide, an organic semiconductor material, or carbon nanotubes, the active layer 17 does not absorb radiation such as X-rays, or if it does absorb any radiation the amount is an extremely minute amount, so the generation of noise in the signal output portion 14 can be effectively suppressed.

Further, in a case where the active layer 17 is formed with carbon nanotubes, the switching speed of the thin-film transistor 10 can be increased, and the thin-film transistor 10 can be formed having a low degree of absorption of light in the visible light range. In the case of forming the active layer 17 with carbon nanotubes, the performance of the thin-film transistor 10 drops significantly simply by mixing an infinitesimal amount of a metal impurity into the active layer 17, so it is necessary to separate, extract, and form extremely high-purity carbon nanotubes by centrifugal separation or the like.

Here, the amorphous oxide, organic semiconductor material, or carbon nanotubes configuring the active layer 17 of the thin-film transistor 10 and the organic photoelectric conversion material configuring the photoelectric conversion film 4 are all capable of being formed into films at a low temperature. Consequently, the substrate 1 is not limited to a substrate with high heat resistance, such as a semiconductor substrate, a quartz substrate, or a glass substrate, and a plastic or other flexible substrate, aramids, or bionanofibers can also be used. Specifically, polyester, such as polyethylene terephthalate, polybutylene phthalate, and polyethylene naphthalate, polystyrene, polycarbonate, polyethersulphone, polyarylate, polyimide, polycyclic olefin, norbornene resin, and poly(chloro-trifluoro-ethylene) or other flexible substrates can be used. By employing a flexible substrate made of plastic, the substrate can be made lightweight, which is advantageous for portability, for example.

Further, an insulating layer for ensuring insulation, a gas barrier layer for preventing the transmission of moisture and oxygen, an undercoat layer for improving flatness or adhesion to the electrodes or the like, and other layers may also be disposed on the substrate 1.

High-temperature processes of 200 degrees or higher can be applied to aramids, so a transparent electrode material can be hardened at a high temperature and given a low resistance, and aramids can also accommodate automatic mounting of driver ICs including solder reflow processes. Further, aramids have a thermal expansion coefficient that is close to that of indium tin oxide (ITO) or a glass substrate, so they have little warping after manufacture and do not break easily. Further, aramids can also form a thinner substrate compared to a glass substrate or the like. An ultrathin glass substrate and an aramid may also be layered to form a substrate.

Further, bionanofibers are composites of cellulose microfibril bundles (bacterial cellulose) that a bacterium (*Acetobacter xylinum*) produces and a transparent resin. Cellulose microfibril bundles have a width of 50 nm, which is a size that is 1/10 with respect to visible light wavelengths, and have high strength, high elasticity, and low thermal expansion. By impregnating and hardening a transparent resin such as an acrylic resin or an epoxy resin in bacterial cellulose, bionanofibers exhibiting a light transmittance of about 90% at a wavelength of 500 nm while including fibers at 60 to 70% can be obtained. Bionanofibers have a low thermal expansion coefficient (3 to 7 ppm) comparable to silicon crystal, a strength comparable to steel (460 MPa), high elasticity (30 GPa), and are flexible, so they can form a thinner substrate 1 compared to a glass substrate or the like.

In the present embodiment, a TFT substrate 30 is formed by sequentially forming the signal output portions 14, the sensor portions 13, and the transparent insulating film 7 on the substrate 1, and the radiation detector 20 is formed by adhering the scintillator 8 onto the TFT substrate 30 using, for example, an adhesive resin whose light absorbance is low.

Figure 5:
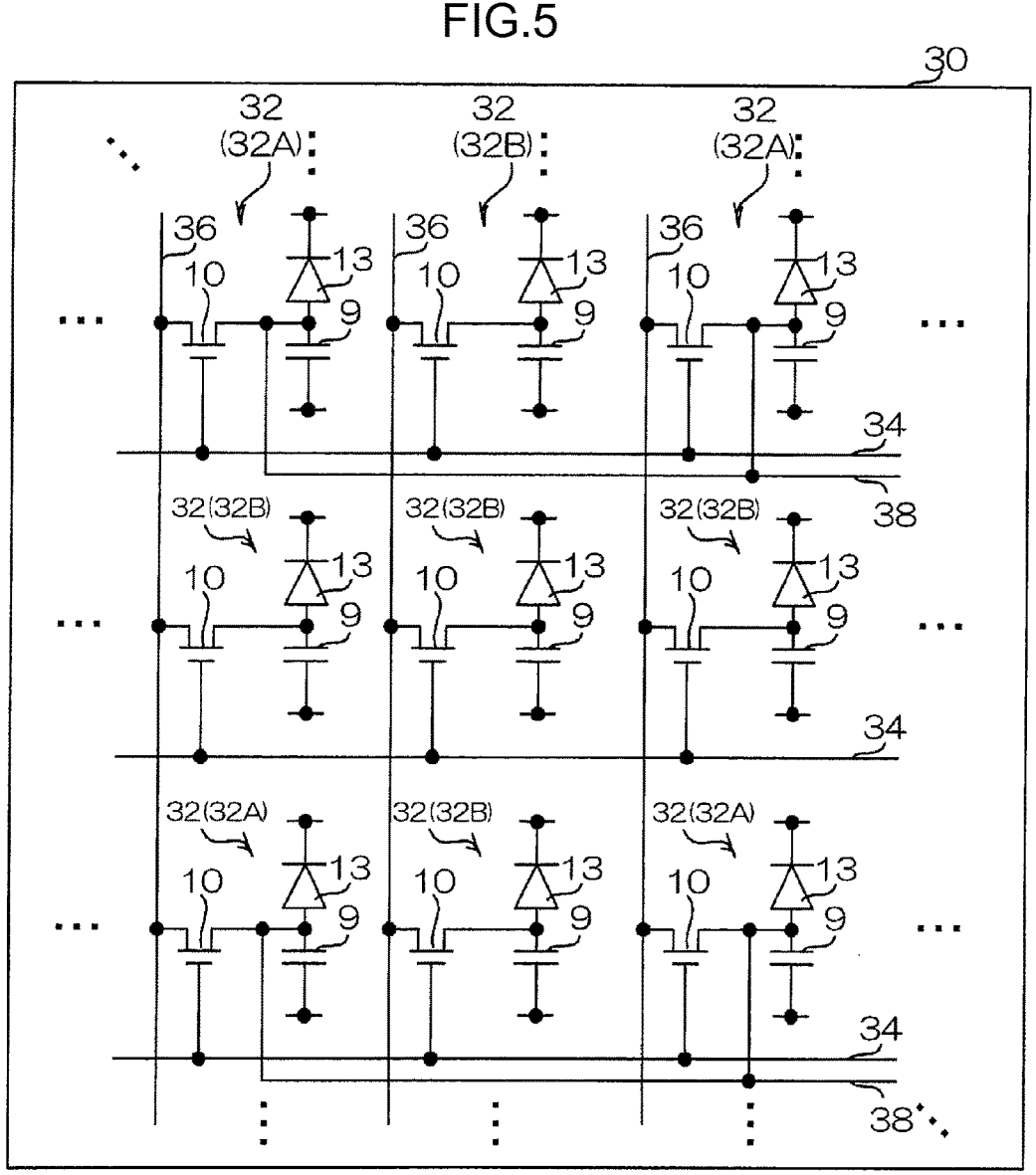
FIG. 5 is a plan view showing the configuration of the radiation detector pertaining to the embodiment.

As shown in FIG. 5, on the TFT substrate 30, pixels 32 configured to include the sensor portions 13, the capacitors 9, and the thin-film transistors 10 are plurally disposed two-dimensionally in one direction (a row direction in FIG. 5) and an intersecting direction (a column direction in FIG. 5) with respect to the one direction.

Further, plural gate lines 34 that are disposed extending in the one direction (the row direction) and are for switching on and off the thin-film transistors 10 and plural data lines 36 that are disposed extending in the intersecting direction (the column direction) and are for reading out the electric charges via the thin-film transistors 10 in an on-state are disposed in the radiation detector 20.

The radiation detector 20 is formed in a tabular, quadrilateral shape having four sides on its outer edges in a plan view; more specifically, the radiation detector 20 is formed in a rectangular shape.

Here, in the radiation detector 20 pertaining to the present embodiment, some of the pixels 32 are used for detecting the state of application of the radiation, and the remaining pixels 32 capture radiographic images. Hereinafter, the pixels 32 for detecting the state of application of the radiation will be called radiation detection pixels 32A, and the remaining pixels 32 will be called radiographic image acquisition pixels 32B.

The radiation detector 20 pertaining to the present embodiment cannot obtain pixel information of radiographic images in the positions where the radiation detection pixels 32A are arranged because the radiation detector 20 captures radiographic images with the radiographic image acquisition pixels 32B excluding the radiation detection pixels 32A of the pixels 32. For this reason, in the radiation detector 20 pertaining to the present embodiment, the radiation detection pixels 32A are arranged in such a way as to be dispersed, and the console 110 executes defective pixel correction processing created by interpolating pixel information of radiographic images in the positions where the radiation detection pixels 32A are arranged using pixel information that has been obtained by the radiographic image acquisition pixels 32B positioned around those radiation detection pixels 32A.

Here, the imaging system 104 pertaining to the present embodiment performs imaging with the part to be imaged having been positioned at least in the central portion of the imaging region in the case of performing imaging using the entire imaging region resulting from the radiation detector 20, such as a case where the part to be imaged is an abdomen or the like, and in the case of performing imaging using only part of the imaging region resulting from the radiation detector 20, such as a case where the part to be imaged is a leg, an arm, a hand, or the like.

Figure 6:
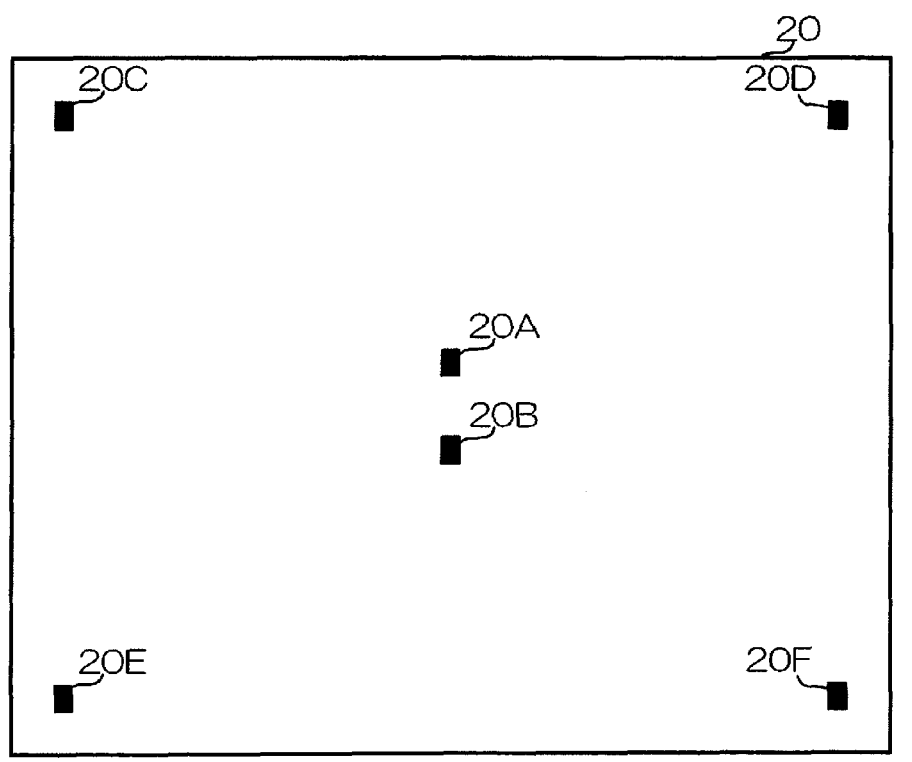
FIG. 6 is a plan view showing an arrangement of radiation detection pixels pertaining to the embodiment.

In the radiation detector 20 pertaining to the present embodiment, as schematically shown in FIG. 6 for example, the radiation detection pixels 32A are arranged in regions (hereinafter called "central portion detection regions") 20A and 20B in the neighborhood of the central portion of the imaging region of the radiation detector 20 and regions (hereinafter called "peripheral edge portion detection regions") 20C to 20F in the neighborhoods of the four corners of the peripheral edge portion of the imaging region.

Additionally, in order to detect the state of application of the radiation, the electronic cassette 40 pertaining to the present embodiment is disposed with a radiation dose acquisition function for acquiring information (hereinafter called "radiation dose information") indicating the applied dose of the radiation X from the radiation source 121.

For this reason, in the radiation detector 20 pertaining to the present embodiment, as shown in FIG. 5, direct read-out lines 38, to which connecting portions between the capacitors 9 and the thin-film transistors 10 in the radiation detection pixels 32A are connected and which are for directly reading out the electric charges stored in those capacitors 9, are disposed extending in the one direction (the row direction). In the radiation detector 20 pertaining to the present embodiment, one direct read-out line 38 is allocated with respect to plural radiation detection pixels 32A arranged side by side in the one direction, and the connecting portions between the capacitors 9 and the thin-film transistors 10 in those plural radiation detection pixels 32A are connected to a common (single) direct read-out line 38. The direct read-out lines correspond to dedicated lines in the claims.

Figure 7:
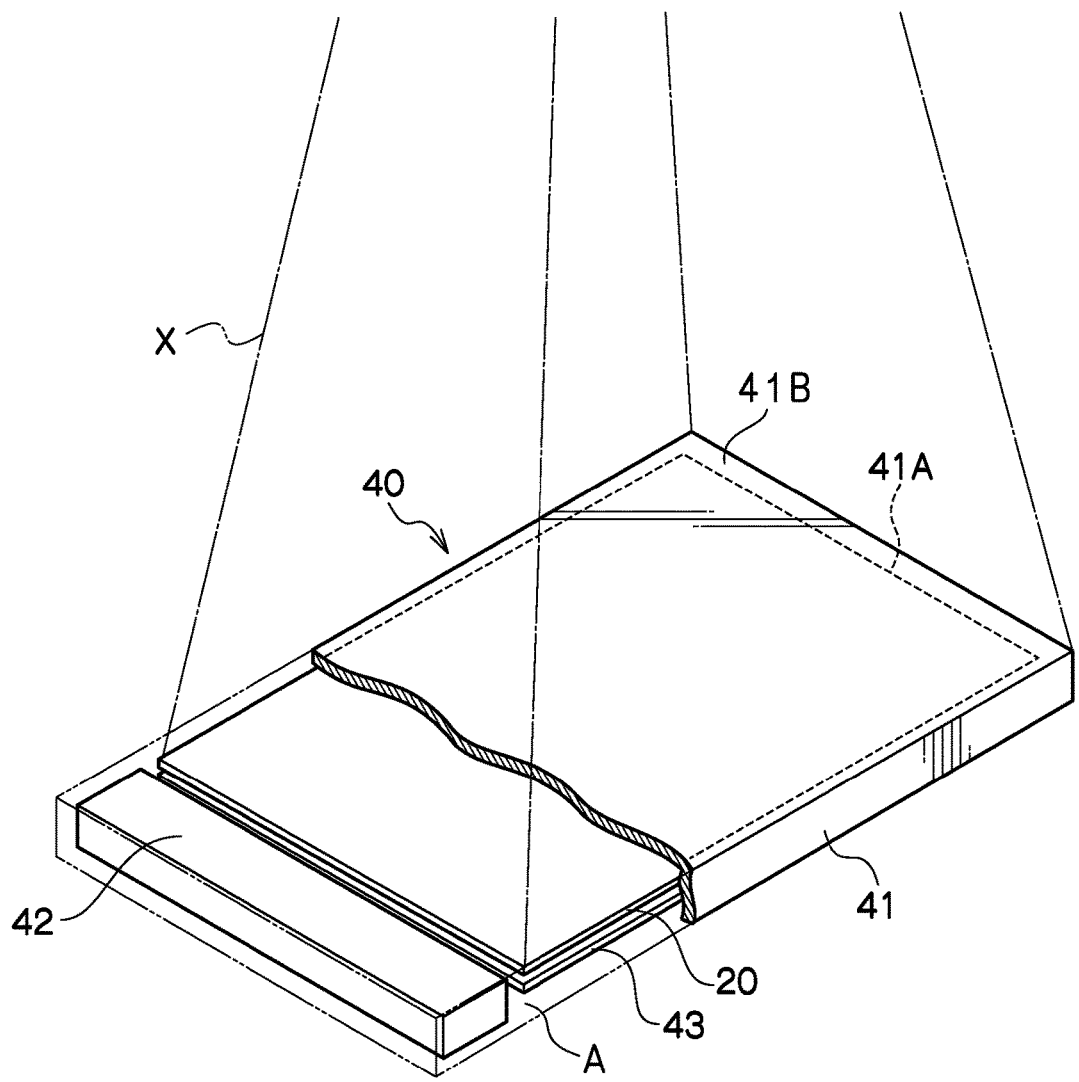
FIG. 7 is a perspective view showing the configuration of an electronic cassette pertaining to the embodiment.

Next, the configuration of the electronic cassette 40 pertaining to the present embodiment will be described. In FIG. 7, there is shown a perspective view showing the configuration of the electronic cassette 40 pertaining to the present embodiment.

As shown in FIG. 7, the electronic cassette 40 pertaining to the present embodiment includes a casing 41 including a material that allows radiation to pass through, and the electronic cassette 40 is given a waterproof and airtight structure. When the electronic cassette 40 is used in an operating room or the like, there is the concern that blood or other contaminants may adhere to the electronic cassette 40. Therefore, by giving the electronic cassette 40 a waterproof and airtight structure and sterilizing the electronic cassette 40 as needed, one electronic cassette 40 can be used repeatedly.

A space A that accommodates various parts is formed inside the casing 41, and the radiation detector 20 that detects the radiation X that has passed through the subject and a lead plate 43 that absorbs backscatter rays of the radiation X are sequentially disposed inside the space A from an irradiated surface side of the casing 41 to which the radiation X is applied.

Here, in the electronic cassette 40 pertaining to the present embodiment, the region of one surface of the tabular shape of the casing 41 corresponding to the position where the radiation detector 20 is disposed is a quadrilateral imaging region 41A capable of detecting the radiation. The surface of the casing 41 having the imaging region 41A is a top panel 41B of the electronic cassette 40, and in the electronic cassette 40 pertaining to the present embodiment, the radiation detector 20 is placed in such a way that the TFT substrate 30 is on the top panel 41B side, and the radiation detector 20 is adhered to the inside surface of the top panel 41B (the surface of the top panel 41B on the opposite side of the surface on which the radiation is made incident) in the casing 41.

As shown in FIG. 7, a case 42 that accommodates a later-described cassette controller 58 and power source 70 (see FIG. 9 for both) is placed on one end side of the inside of the casing 41 in a position that does not coincide with the radiation detector 20 (outside the range of the imaging region 41A). The cassette controller 58 corresponds to an acquiring unit and a detecting unit in the claims.

The casing 41 is configured by carbon fiber, aluminum, magnesium, bionanofibers (cellulose microfibrils), or a composite material, for example, in order to make the entire electronic cassette 40 lightweight.

As the composite material, for example, a material including reinforced fiber resin is used, and carbon, cellulose, or the like is included in the reinforced fiber resin. Specifically, as the composite material, carbon fiber reinforced plastic (CFRP), a composite material with a structure where a foam material is sandwiched by CFRP, or a composite material where the surface of a foam material is coated with CFRP is used. In the present embodiment, a composite material with a structure where a foam material is sandwiched by CFRP is used. Because of this, the strength (rigidity) of the casing 41 can be raised compared to a case where the casing 41 is configured by a carbon alone.

Figure 8:
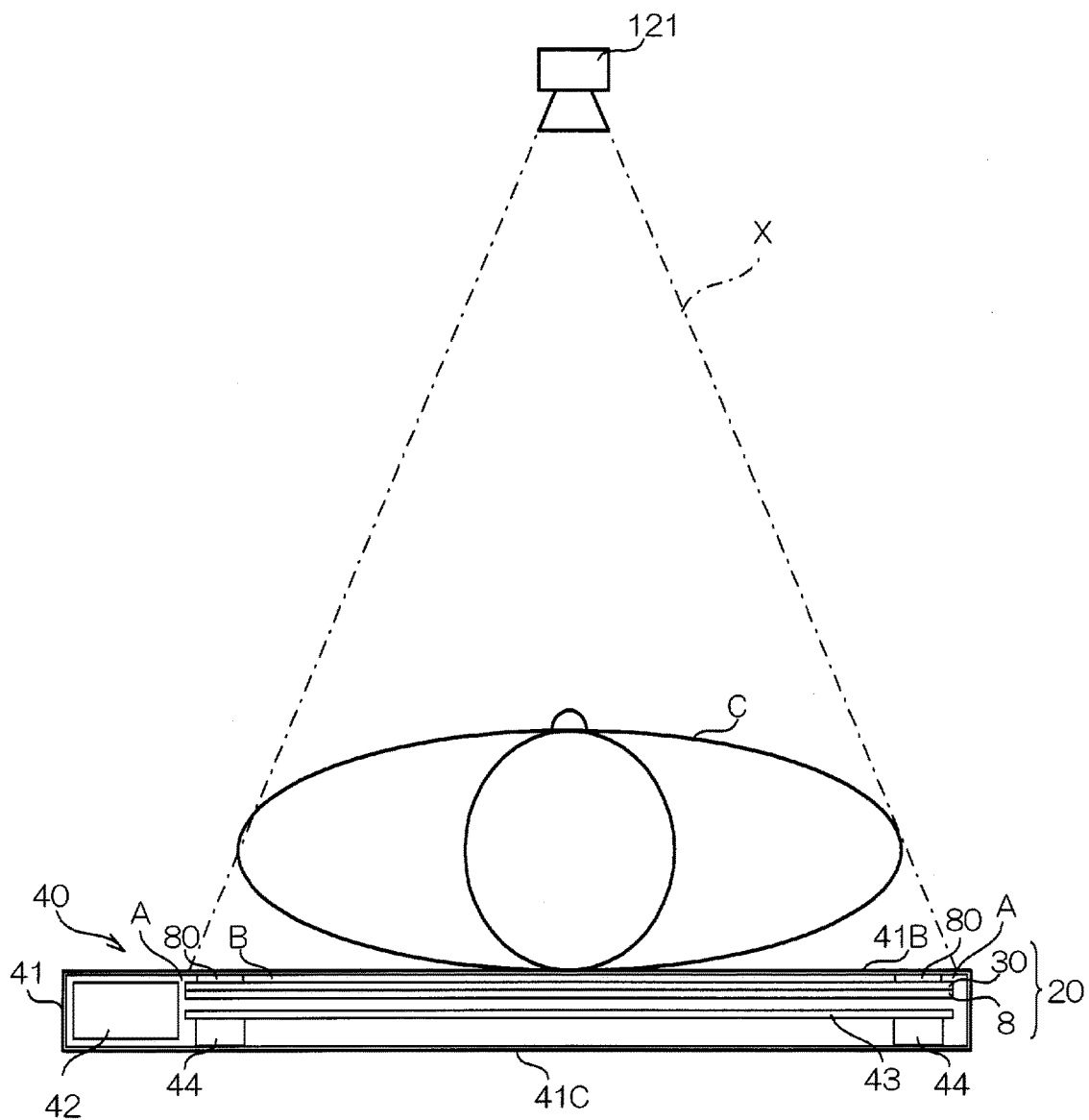
FIG. 8 is a cross-sectional side view showing the configuration of the electronic cassette pertaining to the embodiment.

As shown in FIG. 8, inside the casing 41, supports 44 are disposed on the inner surface of a back surface portion 41C opposing the top panel 41B, and the radiation detector 20 and the lead plate 43 are placed side by side in this order in the application direction of the radiation X between the supports 44 and the top panel 41B. The supports 44 are configured by a foam material, for example, from the standpoint of reducing weight and the standpoint of absorbing dimensional deviations, and the supports 44 support the lead plate 43.

As shown in FIG. 8, adhesive members 80 that detachably adhere the TFT substrate 30 of the radiation detector 20 are disposed on the inner surface of the top panel 41B. Double-sided tape, for example, is used as the adhesive members 80. In this case, the double-sided tape is formed in such a way that the adhesive force of one adhesive surface is stronger than the adhesive force of the other adhesive surface.

Specifically, the surface whose adhesive force is weak (the weak adhesive surface) is set to have a 180° peel strength equal to or less than 1.0 N/cm. Additionally, the surface whose adhesive force is strong (the strong adhesive surface) contacts the top panel 41B, and the weak adhesive surface contacts the TFT substrate 30. Because of this, the thickness of the electronic cassette 40 can be made thinner compared to a case where the radiation detector 20 is fixed to the top panel 41B by, for example, fixing members such as screws. Further, even if the top panel 41B deforms due to an impact or a load, the radiation detector 20 follows the deformation of the top panel 41B whose rigidity is high, so only large curvature (a gentle curve) arises and the potential for the radiation detector 20 to break due to localized low curvature becomes lower. Moreover, the radiation detector 20 contributes to improving the rigidity of the top panel 41B.

In this way, in the electronic cassette 40 pertaining to the present embodiment, the radiation detector 20 is adhered to the inside of the top panel 41B of the casing 41, so the casing 41 is made separable into two between the top panel 41B side and the back surface portion 41C side, and when the radiation detector 20 is adhered to the top panel 41B or when the radiation detector 20 is detached from the top panel 41B, the casing 41 is separated into two between the top panel 41B side and the back surface portion 41C side.

In the present embodiment, the adhesion of the radiation detector 20 to the top panel 41B does not have to be performed in a clean room or the like. The reason is because, in a case where foreign materials such as metal fragments that absorb radiation have become mixed in between the radiation detector 20 and the top panel 41B, the foreign materials can be removed by detaching the radiation detector 20 from the top panel 41B.

Next, the configurations of relevant portions of an electrical system of the imaging system 104 pertaining to the present embodiment will be described with reference to FIG. 9.

Figure 9:
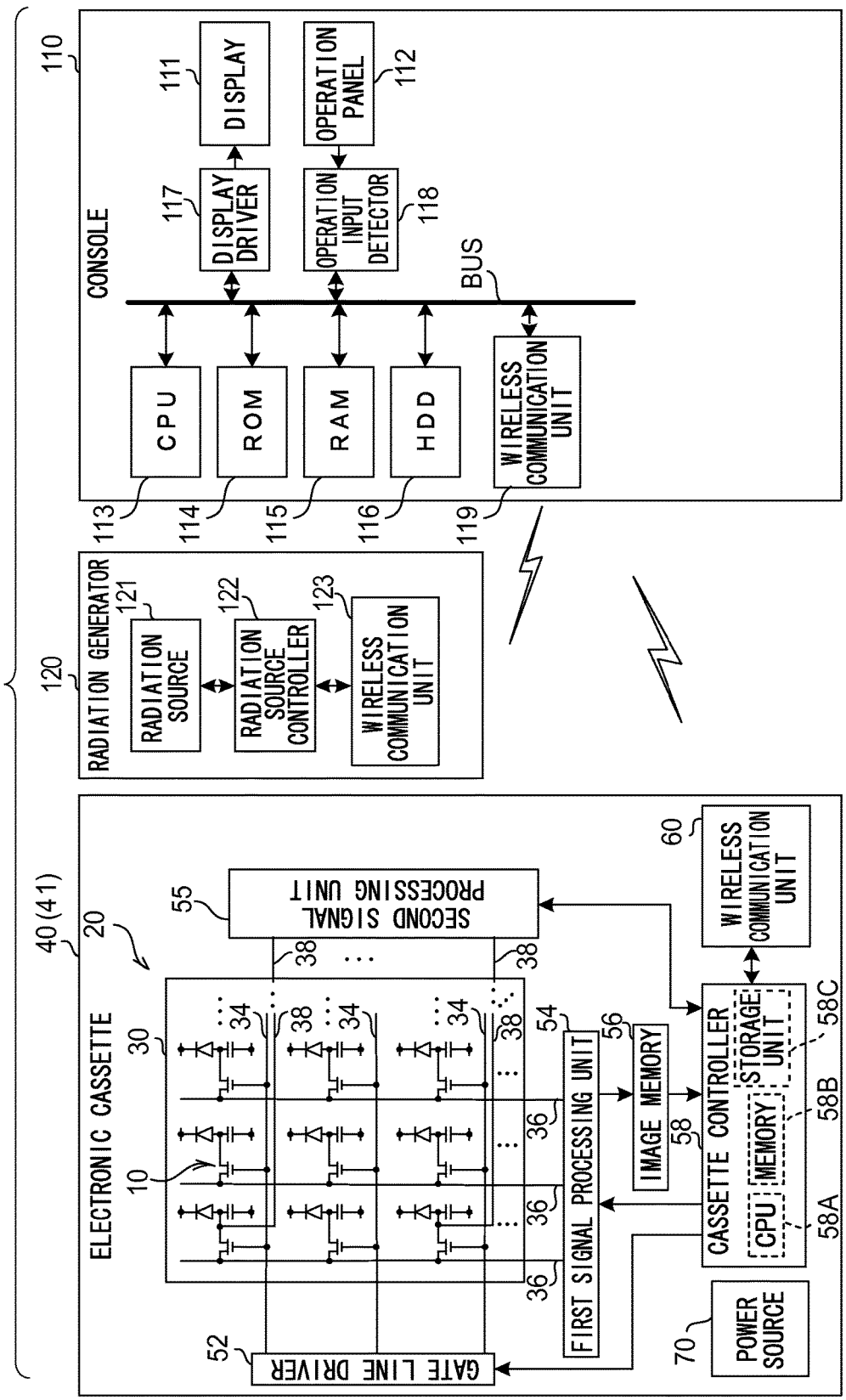
FIG. 9 is a block diagram showing the configurations of main portions of an electrical system of the radiographic imaging system pertaining to the embodiment.

As shown in FIG. 9, in the radiation detector 20 built into the electronic cassette 40, a gate line driver 52 is placed on one side of two sides adjacent to each other, and a first signal processing unit 54 is placed on the other side. The individual gate lines 34 of the TFT substrate 30 are connected to the gate line driver 52, and the individual data lines 36 of the TFT substrate 30 are connected to the first signal processing unit 54.

Further, an image memory 56, a cassette controller 58, and a wireless communication unit 60 are disposed inside the casing 41.

The thin-film transistors 10 of the TFT substrate 30 are sequentially switched on in row units by signals supplied via the gate lines 34 from the gate line driver 52. The electric charges that have been read out by the thin-film transistors 10 switched to an on-state are transmitted through the data lines 36 as electrical signals and are input to the first signal processing unit 54. Because of this, the electric charges are sequentially read out in row units, and a two-dimensional radiographic image becomes acquirable.

Although it is not shown in the drawings, the first signal processing unit 54 includes amplifier circuits that amplify the input electrical signals and sample-and-hold circuits for each of the individual data lines 36, and the electrical signals that have been transmitted through the individual data lines 36 are amplified by the amplifier circuits and are thereafter held in the sample-and-hold circuits. Further, a multiplexer and an analog-to-digital (A/D) converter are sequentially connected to the output sides of the sample-and-hold circuits, and the electrical signals held in the individual sample-and-hold circuits are sequentially (serially) input to the multiplexer and are converted into digital image data by the A/D converter.

The image memory 56 is connected to the first signal processing unit 54, and the image data that have been output from the A/D converter of the first signal processing unit 54 are sequentially stored in the image memory 56. The image memory 56 has a storage capacity capable of storing a predetermined number of frames of image data, and each time radiographic imaging is performed, the image data obtained by the imaging are sequentially stored in the image memory 56.

The image memory 56 is also connected to the cassette controller 58. The cassette controller 58 is configured to include a microcomputer, includes a central processing unit (CPU) 58A, a memory 58B including a read-only memory (ROM) and a random access memory (RAM), and a non-volatile storage unit 58C including a flash memory or the like, and controls the actions of the entire electronic cassette 40.

Moreover, the wireless communication unit 60 is connected to the cassette controller 58. The wireless communication unit 60 is adapted to a wireless local area network (LAN) standard represented by IEEE (Institute of Electrical and Electronics Engineers) 802.11a/b/g or the like and controls the transmission of various types of information between the electronic cassette 40 and external devices by wireless communication. Via the wireless communication unit 60, the cassette controller 58 is made capable of wireless communication with an external device such as the console 110 that performs control relating to radiographic imaging and is made capable of transmitting and receiving various types of information to and from the console 110 and the like.

Further, a power source 70 is disposed in the electronic cassette 40, and the various circuits and elements described above (the gate line driver 54, the first signal processing unit 54, the image memory 56, the wireless communication unit 60, the microcomputer functioning as the cassette controller 58, etc.) operate on power supplied from the power source 70. The power source 70 has a built-in battery (a rechargeable secondary battery) so as to not impair the portability of the electronic cassette 40, and the power source 70 supplies power to the various circuits and elements from the charged battery. In FIG. 9, illustration of wires connecting the various circuits and elements to the power source 70 is omitted.

In the radiation detector 20 pertaining to the present embodiment, a second signal processing unit 55 is placed on the opposite side of the gate line driver 52 across the TFT substrate 30 in order to realize the radiation dose acquisition function, and the individual direct read-out lines 38 of the TFT substrate 30 are connected to the second signal processing unit 55.

Figure 10:
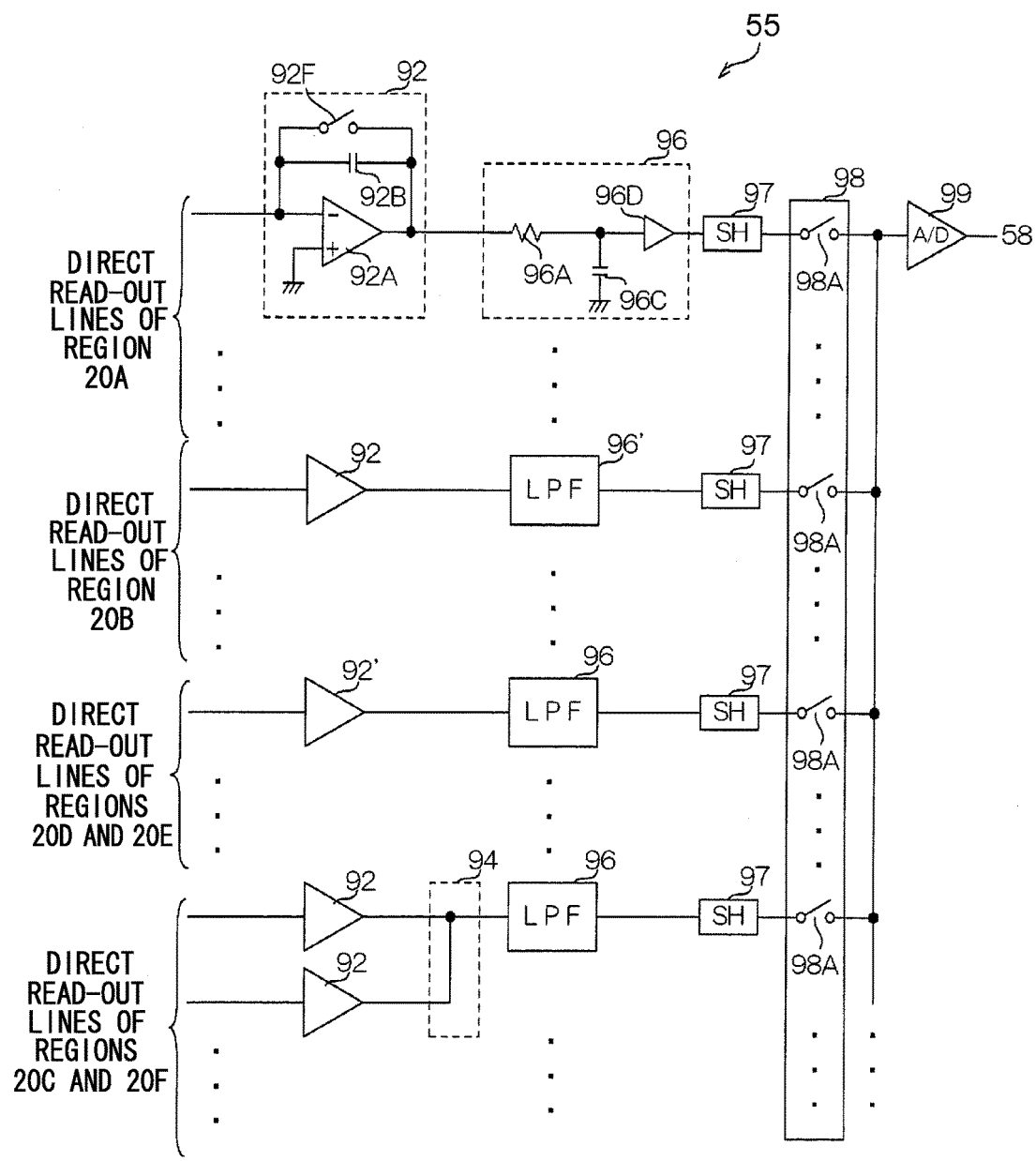
FIG. 10 is a circuit diagram showing the configuration of a second signal processing unit pertaining to the embodiment.

Here, the configuration of the second signal processing unit 55 pertaining to the present embodiment will be described. In FIG. 10, there is shown a circuit diagram showing the configuration of the second signal processing unit 55 pertaining to the present embodiment.

As shown in FIG. 10, the second signal processing unit 55 pertaining to the present embodiment includes variable gain pre-amps (charge amps) 92, low-pass filters (LPFs) 96, and sample-and-hold circuits 97 in correspondence to each of the direct read-out lines 38 connected to the radiation detection pixels 32A disposed in the central portion detection region 20A. The variable gain pre-amps (charge amps) 92 correspond to amplifiers in the claims, and the low-pass filters (LPFs) 96 correspond to low-pass filters in the claims.

Each of the variable gain pre-amps 92 is configured to include an op-amp 92A whose positive input side is grounded, a capacitor 92B that is connected in parallel between the negative input side and the output side of the op-amp 92A, and a reset switch 92F. The reset switches 92F are switched by the cassette controller 58. Further, each of the LPFs 96 is configured to include a resistor 96A and a capacitor 96C.

The second signal processing unit 55 pertaining to the present embodiment also includes variable gain pre-amps 92, LPFs 96' whose low-pass frequency differs from that of the LPFs 96, and sample-and-hold circuits 97 in correspondence to each of the direct read-out lines 38 connected to the radiation detection pixels 32A disposed in the central portion detection region 20B. In the present embodiment, low-pass filters whose low-pass frequency is lower than that of the LPFs 96 are applied as the LPFs 96'. The LPFs (low-pass filters) 96' correspond to low-pass filters in the claims.

Further, the second signal processing unit 55 pertaining to the present embodiment also includes variable gain pre-amps 92' whose gain differs from that of the variable gain pre-amps 92, LPFs 96, and sample-and-hold circuits 97 in correspondence to each of the direct read-out lines 38 connected to the radiation detection pixels 32A disposed in the peripheral edge portion detection regions 20D and 20E. In the present embodiment, variable gain pre-amps whose gain is higher than that of the variable gain pre-amps 92 are applied as the variable gain pre-amps 92'. The variable gain pre-amps 92' correspond to amplifiers in the claims.

Moreover, the second signal processing unit 55 pertaining to the present embodiment also includes variable gain pre-amps 92, binning components 94, LPFs 96, and sample-and-hold circuits 97 in correspondence to each of the direct read-out lines 38 connected to the radiation detection pixels 32A disposed in the peripheral edge portion detection regions 20C and 20F. The binning components 94 synthesize, into one electrical signal, the electrical signals that have been output from a predetermined number (in the present embodiment, two) of the direct read-out lines 38. The binning components 94 correspond to a synthesizing unit in the claims.

Additionally, the second signal processing unit 55 pertaining to the present embodiment includes one multiplexer 98 and one A/D converter 99 each. The sample timings of the sample-and-hold circuits 97 and outputs selected by switches 98A disposed in the multiplexer 98 are also switched by the cassette controller 58.

The direct read-out lines 38 connected to the radiation detection pixels 32A disposed in the central portion detection regions 20A and 20B and the peripheral edge portion detection regions 20D and 20E are individually connected to the input ends of the multiplexer 98 via the order of the corresponding variable gain pre-amps 92 or variable gain pre-amps 92', LPFs 96 or LPFs 96', and sample-and-hold circuits 97.

Further, the direct read-out lines 38 connected to the radiation detection pixels 32A disposed in the peripheral edge portion detection regions 20C and 20F are individually connected to the input ends of the multiplexer 98 via the order of the corresponding variable gain pre-amps 92, binning components 94, LPFs 96, and sample-and-hold circuits 97. Additionally, the output ends of the multiplexer 98 are connected to the input end of the A/D converter 99, and the output end of the A/D converter 99 is connected to the cassette controller 58.

When causing the radiation dose acquisition function to work, the cassette controller 58 first discharges (resets) the electric charges stored in the capacitors 92B by switching the reset switches 92F of the variable gain pre-amps 92 and 92' to an on-state for a predetermined period of time.

The electric charges stored in the capacitors 9 of the radiation detection pixels 32A as a result of the radiation X being applied are transmitted as electrical signals through the connected direct read-out lines 38. The electrical signals transmitted through the direct read-out lines 38 are amplified at predetermined gains by the corresponding variable gain pre-amps 92 and 92', thereafter the electrical signals corresponding to the radiation detection pixels 32A disposed in the peripheral edge portion detection regions 20C and 20F are synthesized by the binning components 94, and filtering is performed at predetermined low-pass frequencies by the LPFs 96 and 96'.

After performing the discharge (reset), the cassette controller 58 causes the sample-and-hold circuits 97 to hold the signal levels of the filtered electrical signals by driving the sample-and-hold circuits 97 for a predetermined period of time.

Then, the signal levels held in the sample-and-hold circuits 97 are sequentially selected by the multiplexer 98 in accordance with the control by the cassette controller 58 and are converted from analog to digital by the A/D converter 99; thereafter, the digital signals obtained thereby are output to the cassette controller 58. The digital signals output from the A/D converter 99 represent the dose of radiation that was applied in the predetermined period of time with respect to the radiation detection pixels 32A and correspond to the radiation dose information.

Additionally, the cassette controller 58 sequentially stores, in a predetermined region of the RAM in the memory 58B, the radiation dose information that has been input from the A/D converter 99.

As shown in FIG. 9, the console 110 is configured as a server computer and includes a display 111, which displays operation menus, captured radiographic images, and so forth, and an operation panel 112, which is configured to include plural keys and to which various types of information and operation instructions are input.

Further, the console 110 pertaining to the present embodiment includes a CPU 113 that controls the actions of the entire device, a ROM 114 in which various programs including a control program are stored beforehand, a RAM 115 that temporarily stores various types of data, a hard disk drive (HDD) 116 that stores and holds various types of data, a display driver 117 that controls the display of various types of information on the display 111, and an operation input detector 118 that detects states of operation with respect to the operation panel 112. Further, the console 110 includes a wireless communication unit 119 that transmits and receives various types of information such as later-described exposure conditions to and from the radiation generator 120 by wireless communication and also transmits and receives various types of information such as image data to and from the electronic cassette 40 by wireless communication.

The CPU 113, the ROM 114, the RAM 115, the HDD 116, the display driver 117, the operation input detector 118, and the wireless communication unit 119 are connected to each other via a system bus BUS. Consequently, the CPU 113 can access the ROM 114, the RAM 115, and the HDD 116, can control the display of various types of information on the display 111 via the display driver 117, and can control the transmission and reception of various types of information to and from the radiation generator 120 and the electronic cassette 40 via the wireless communication unit 119. Further, the CPU 113 can grasp states of operation by a user with respect to the operation panel 112 via the operation input detector 118.

The radiation generator 120 includes the radiation source 121, a wireless communication unit 123 that transmits and receives various types of information such as the exposure conditions to and from the console 110, and a radiation source controller 122 that controls the radiation source 121 on the basis of the received exposure conditions.

The radiation source controller 122 is also configured to include a microcomputer and stores the received exposure conditions and so forth. The exposure conditions received from the console 110 include information such as tube voltage, tube current, and so forth. The radiation source controller 122 causes the radiation X to be applied from the radiation source 121 on the basis of the received exposure conditions.

Next, the action of the imaging system 104 pertaining to the present embodiment will be described.

Figure 11:
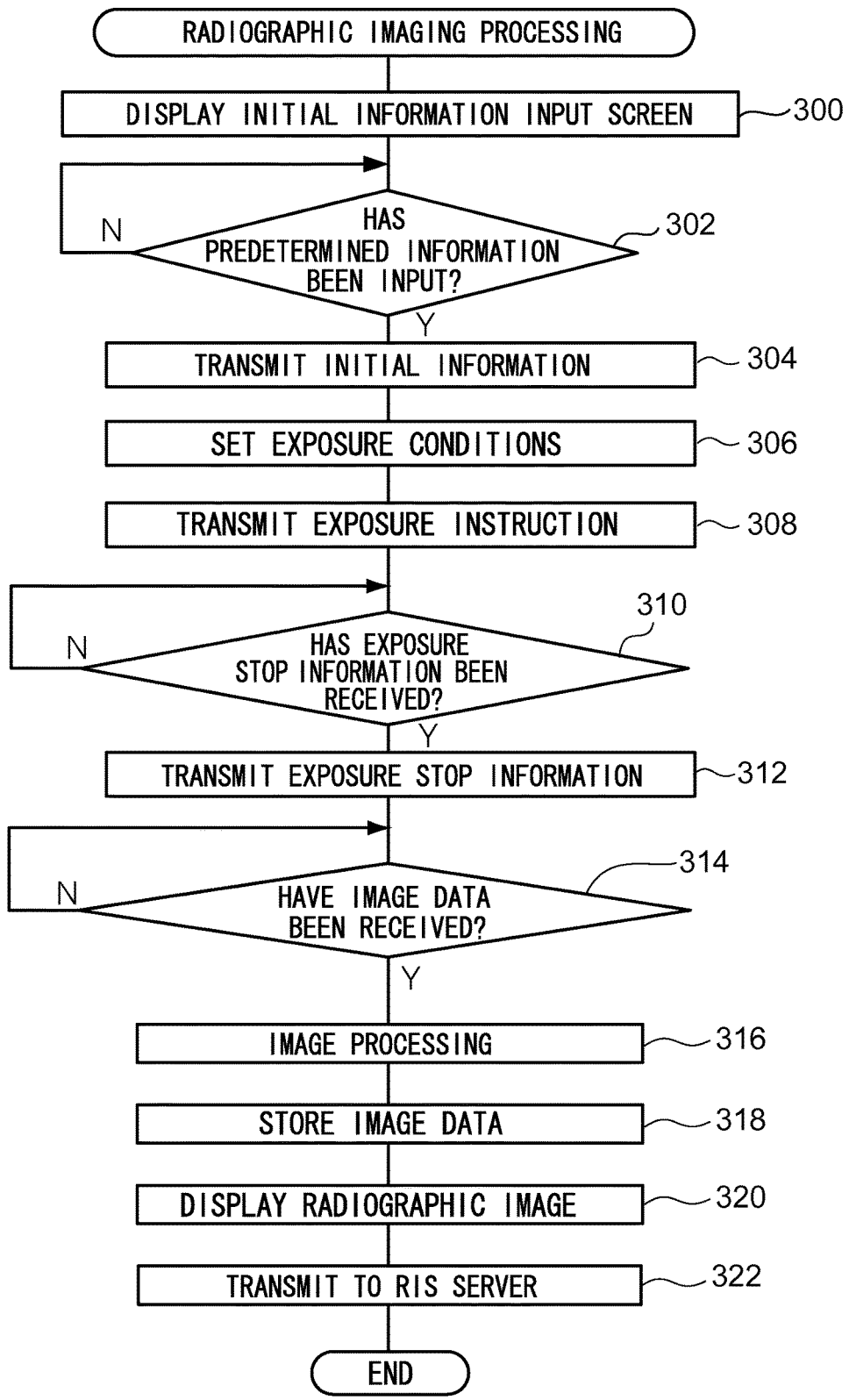
FIG. 11 is a flowchart showing a flow of processing by a radiographic imaging processing program pertaining to the embodiment.

First, the action of the console 110 when capturing a radiographic image will be described with reference to FIG. 11. FIG. 11 is a flowchart showing a flow of processing by a radiographic imaging processing program executed by the CPU 113 of the console 110 when an instruction to execute the program has been input via the operation panel 112; this program is stored beforehand in a predetermined region of the ROM 114.

In step 300 of FIG. 11, the CPU 113 controls the display driver 117 so as to cause the display 111 to display a predetermined initial information input screen, and in the next step 302, the CPU 113 waits for the input of predetermined information.

In FIG. 12, there is shown an example of the initial information input screen displayed by the display 111 by the processing of step 300. As shown in FIG. 12, in the initial information input screen pertaining to the present embodiment, a message prompting the user to input the name of the subject on which radiographic imaging is to be performed, the part to be imaged, the posture during imaging, and the exposure conditions for exposure to the radiation X during imaging (in the present embodiment, the tube voltage and the tube current when exposing the subject to the radiation X), and input fields for inputting these pieces of information, are displayed.

When the initial information input screen shown in FIG. 12 is displayed on the display 111, the radiographer inputs the name of the subject to be imaged, the part to be imaged, the posture during imaging, and the exposure conditions into the corresponding input fields via the operation panel 112.

Then, in a case where the posture during imaging is the upright position or the recumbent position, the radiographer puts the electronic cassette 40 into the corresponding holder 162 of the upright-position stand 160 or holder 166 of the recumbent-position table 164, positions the radiation source 121 in the corresponding position, and thereafter positions the subject in a predetermined imaging position. With respect to this, in a case where the part to be imaged is an arm, a leg, or the like and imaging is to be performed without putting the electronic cassette 40 into a holder, the radiographer positions the subject, the electronic cassette 40, and the radiation source 121 so that the part to be imaged is capable of being imaged. Thereafter, the radiographer designates, via the operation panel 112, the end button displayed in the neighborhood of the lower end of the initial information input screen. When the end button is designated by the radiographer, the determination in step 302 becomes YES and the processing moves to step 304.

In step 304, the information (hereinafter called "initial information") that has been input on the initial information input screen is transmitted to the electronic cassette 40 via the wireless communication unit 119, and thereafter, in the next step 306, the exposure conditions included in the initial information is transmitted to the radiation generator 120 via the wireless communication unit 119 to thereby set the exposure conditions. In response to this, the radiation source controller 122 of the radiation generator 120 prepares for exposure in the received exposure conditions.

In the next step 308, the instruction information instructing the start of exposure is transmitted to the radiation generator 120 and the electronic cassette 40 via the wireless communication unit 119.

In response to this, the radiation source 121 starts emitting the radiation X at the tube voltage and tube current corresponding to the exposure conditions that the radiation generator 120 received from the console 110. The radiation X emitted from the radiation source 121 passes through the subject and thereafter reaches the electronic cassette 40.

When the cassette controller 58 of the electronic cassette 40 receives the instruction information instructing the start of exposure, the cassette controller 58 acquires the radiation dose information by means of the radiation dose acquisition function and stands by until the radiation dose indicated by the acquired radiation dose information becomes equal to or greater than a first threshold value predetermined as a value for detecting that the application of the radiation has been started. Next, after the electronic cassette 40 has started the action of capturing the radiographic image, the electronic cassette 40 stops the imaging action, and transmits exposure stop information to the console 110, at the point in time when the cumulative value of the radiation dose indicated by the radiation dose information has reached a second threshold value predetermined as a value for stopping the exposure to the radiation X on the basis of the part to be imaged and the exposure conditions included in the initial information.

Thus, in the next step 310, the CPU 113 waits to receive the exposure stop information, and in the next step 312, the instruction information instructing the stopping of the exposure to the radiation X is transmitted to the radiation generator 120 via the wireless communication unit 119. In response to this, the exposure to the radiation X from the radiation source 121 is stopped.

When the electronic cassette 40 stops the action of capturing the radiographic image, the electronic cassette 40 transmits to the console 110 the image data obtained by the imaging.

Thus, in the next step 314, the CPU 113 stands by until the image data are received from the electronic cassette 40, and in the next step 316, the defective pixel correction processing is performed with respect to the received image data and thereafter image processing that performs various types of correction such as shading correction is executed.

In the next step 318, the image data on which the image processing has been performed (hereinafter called "corrected image data") is stored in the HDD 116, and in the next step 320, the display driver 117 is controlled so as to cause the display 111 to display the radiographic image represented by the corrected image data for checking and so forth.

In the next step 322, the corrected image data is transmitted to the RIS server 150 via the in-hospital network 102, and thereafter the radiographic imaging processing program ends. The corrected image data that have been transmitted to the RIS server 150 are stored in the database 150A so that it becomes possible for doctors to read the captured radiographic image and make a diagnosis.

Figure 13:
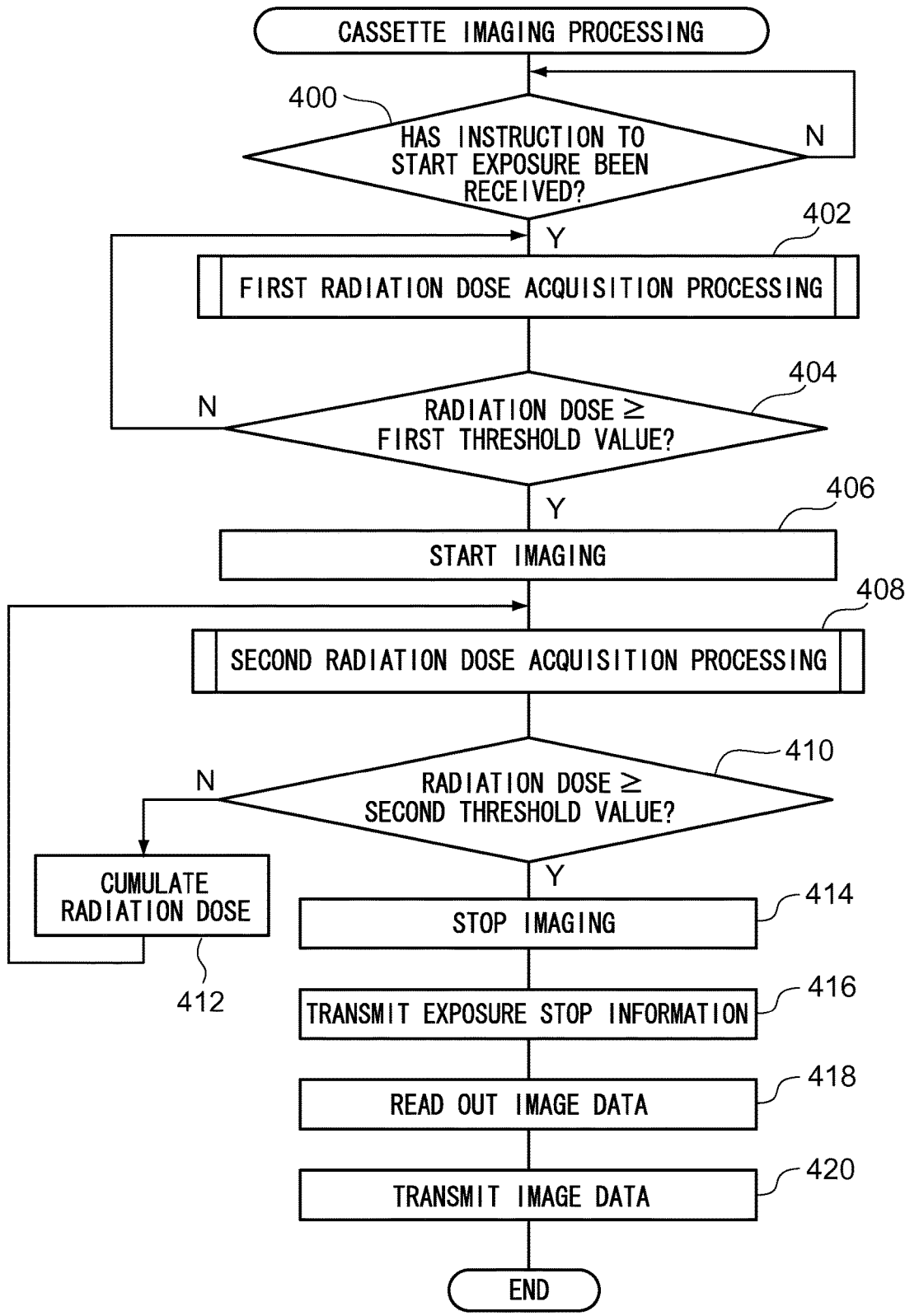
FIG. 13 is a flowchart showing a flow of processing by a cassette imaging processing program pertaining to the embodiment.

Next, the action of the electronic cassette 40 upon having received the initial information from the console 110 will be described with reference to FIG. 13. FIG. 13 is a flowchart showing a flow of processing by a cassette imaging processing program executed by the CPU 58A in the cassette controller 58 of the electronic cassette 40 at this time; this program is stored beforehand in a predetermined region of the memory 58B.

In step 400 of FIG. 13, the CPU 58A waits to receive the instruction information instructing the start of exposure from the console 110, and in the next step 402, a first radiation dose acquisition processing routine program that acquires the radiation dose information by means of the radiation dose acquisition function is executed.

Figure 14:
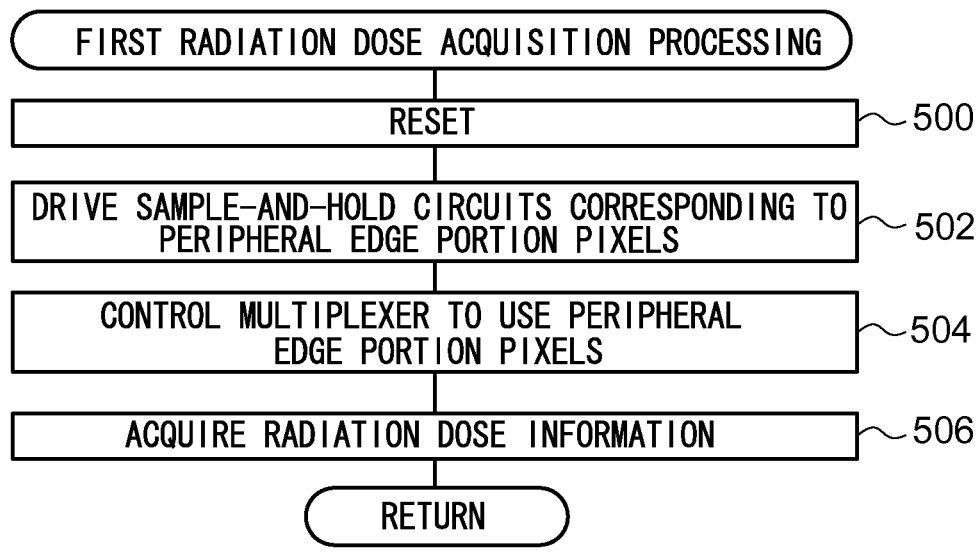
FIG. 14 is a flowchart showing a flow of processing by a first radiation dose acquisition processing routine program pertaining to the embodiment.

The first radiation dose acquisition processing routine program pertaining to the present embodiment will be described below with reference to FIG. 14. FIG. 14 is a flowchart showing a flow of processing by the first radiation dose acquisition processing routine program pertaining to the present embodiment; this program is also stored beforehand in a predetermined region of the memory 58B.

In step 500 of FIG. 14, the electric charges that had been stored in the capacitors 92B is discharged by switching the reset switches 92F of all the variable gain pre-amps 92 and 92' to an on-state for a predetermined period of time and the second signal processing unit 55 is reset by discharging the signal levels held in all the sample-and-hold circuits 97.

In the next step 502, all the sample-and-hold circuits 97 corresponding to the radiation detection pixels 32A of the peripheral edge portion detection regions 20C to 20F (hereinafter called "peripheral edge portion pixels") are driven for a predetermined period of time to thereby cause the sample-and-hold circuits 97 to hold the signal levels of the filtered electrical signals. In the next step 504, the multiplexer 98 is controlled in such a way that the output signals from the sample-and-hold circuits 97 corresponding to the peripheral edge portion pixels are sequentially selected and output.

Because of the above processing, after being amplified by the variable gain pre-amps 92 or the variable gain pre-amps 92', the electrical signals corresponding to the peripheral edge portion pixels of the peripheral edge portion detection regions 20C and 20F are synthesized by the binning components 94, and digital data representing the signal levels of the electrical signals filtered by the LPFs 96 are sequentially output from the A/D converter 99 as the radiation dose information. In the next step 506, the radiation dose information output from the A/D converter 99 is sequentially acquired and thereafter the first radiation dose acquisition processing routine program ends. When the first radiation dose acquisition processing routine program ends, the processing moves to step 404 of the cassette imaging processing program (main routine) shown in FIG. 13.

In step 404, it is determined whether or not the radiation dose (in the present embodiment, the average value of the radiation dose represented by the radiation dose information sequentially output from the A/D converter 99) represented by the information acquired by the processing of step 402 is equal to or greater than the first threshold value. In a case where the determination is NO in step 404, the processing returns to step 402, and in a case where the determination is YES, this is regarded to mean that exposure to the radiation X from the radiation source 121 has been started and moves to step 406.

In step 406, the electric charges stored in the capacitors 9 in the pixels 32 of the radiation detector 20 is discharged and thereafter the storage of the electric charges in the capacitors 9 starts again to thereby start the action of capturing the radiographic image. In the next step 408, a second radiation dose acquisition processing routine program that acquires the radiation dose information is executed by the radiation dose acquisition function.

Figure 15:
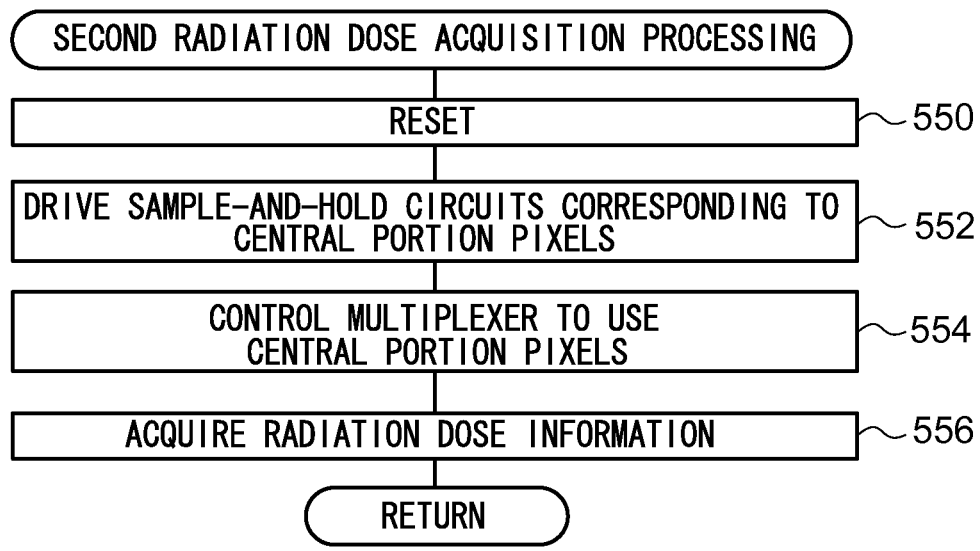
FIG. 15 is a flowchart showing a flow of processing by a second radiation dose acquisition processing routine program pertaining to the embodiment.

The second radiation dose acquisition processing routine program pertaining to the present embodiment will be described below with reference to FIG. 15. FIG. 15 is a flowchart showing a flow of processing by the second radiation dose acquisition processing routine program pertaining to the present embodiment; this program is also stored beforehand in a predetermined region of the memory 58B.

In step 550 of FIG. 15, the electric charges that had been stored in the capacitors 92B is discharged by switching the reset switches 92F of all the variable gain pre-amps 92 and 92' to an on-state for a predetermined period of time and the second signal processing unit 55 is reset by discharging the signal levels held in all the sample-and-hold circuits 97.

In the next step 552, all the sample-and-hold circuits 97 corresponding to the radiation detection pixels 32A of the central portion detection regions 20A and 20B (hereinafter called "center portion pixels") are driven for a predetermined period of time to thereby cause the sample-and-hold circuits 97 to hold the signal levels of the filtered electrical signals. In the next step 554, the multiplexer 98 is controlled in such a way that the output signals from the sample-and-hold circuits 97 corresponding to the center portion pixels are sequentially selected and output.

Because of the above processing, digital data representing the signal levels of the electrical signals filtered by the LPFs 96 or LPFs 96' after being amplified by the variable gain pre-amps 92 are sequentially output from the A/D converter 99 as the radiation dose information. In the next step 556, the radiation dose information output from the A/D converter 99 is sequentially acquired and thereafter the second radiation dose acquisition processing routine program ends. When the second radiation dose acquisition processing routine program ends, the processing moves to step 410 of the cassette imaging processing program (main routine) shown in FIG. 13.

In step 410, it is determined whether or not the radiation dose (in the present embodiment, the average value of the radiation dose represented by the radiation dose information sequentially output from the A/D converter 99) represented by the information acquired by the processing of step 408 is equal to or greater than the second threshold value. In a case where the determination is NO in step 410, the processing moves to step 412, the radiation dose acquired by the processing of step 408 is cumulated, the processing returns to step 408, and moves to step 414 at the point in time when the determination becomes YES. When repeatedly executing the processing of step 408 to step 412, in step 410 it is determined whether or not the radiation dose cumulated up until then has become equal to or greater than the second threshold value.

In step 414, the imaging action started by the processing of step 406 stops. In the next step 416, the exposure stop information is transmitted to the console 110 via the wireless communication unit 60.

In the next step 418, the gate line driver 52 is controlled so as to cause ON signals to be output sequentially one line at a time from the gate line driver 52 to the gate lines 34, and the thin-film transistors 10 connected to the gate lines 34 are sequentially switched on one line at a time.

In the radiation detector 20, when the thin-film transistors 10 connected to the gate lines 34 are sequentially switched on one line at a time, the electric charges stored in the capacitors 9 flow out to the data lines 36 as electrical signals sequentially one line at a time. The electrical signals that have flowed out to the data lines 36 are converted into digital image data by the first signal processing unit 54, and the digital image data are stored in the image memory 56.

Thus, in step 418, the image data stored in the image memory 56 is read out, and in the next step 420, the read image data is transmitted to the console 110 via the wireless communication unit 60 and thereafter the cassette imaging processing program ends.

Incidentally, as shown in FIG. 8, the radiation detector 20 is built into the electronic cassette 40 pertaining to the present embodiment in such a way that the radiation X is applied from the TFT substrate 30 side.

Figure 16:
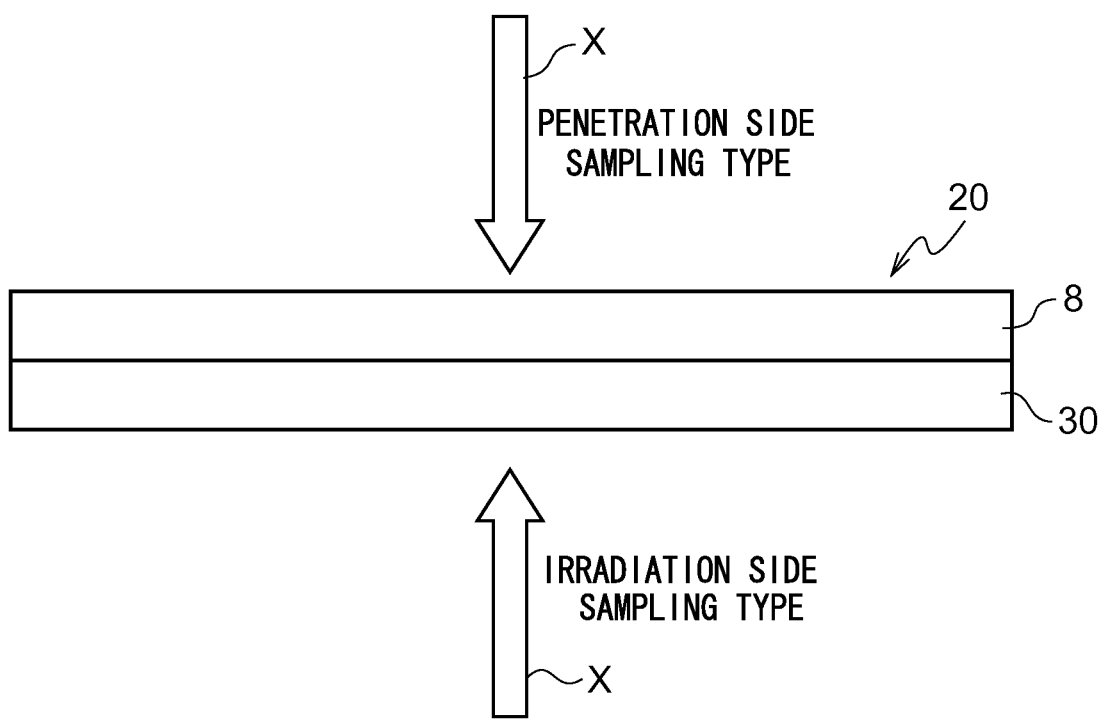
FIG. 16 is a cross-sectional side view for describing an irradiation side sampling method and a penetration side sampling method for reading a radiographic image.

Here, as shown in FIG. 16, in a case where the radiation detector 20 is configured as a so-called penetration side sampling type in which the radiation is applied from the side on which the scintillator 8 is formed and the radiographic image is read by the TFT substrate 30 disposed on the back surface side of the surface on which the radiation is made incident, light is emitted more strongly on the upper surface side of the scintillator 8 in FIG. 16 (the opposite side of the TFT substrate 30 side). Further, in a case where the radiation detector 20 is configured as a so-called irradiation side sampling type in which the radiation is applied from the TFT substrate 30 side and the radiographic image is read by the TFT substrate 30 disposed on the front surface side of the surface on which the radiation is made incident, the radiation that has passed through the TFT substrate 30 is made incident on the scintillator 8, and the TFT substrate 30 side of the scintillator 8 more strongly emits light. In the sensor portions 13 disposed on the TFT substrate 30, electric charges are generated by the light generated by the scintillator 8. For this reason, the emission position of the scintillator 8 with respect to the TFT substrate 30 is closer in a case where the radiation detector 20 is configured as an irradiation side sampling type than in a case where the radiation detector 20 is configured as a penetration side sampling type, so the resolution of the radiographic image obtained by imaging is higher.

Further, in the radiation detector 20, the photoelectric conversion film 4 is configured by an organic photoelectric conversion material, and virtually no radiation is absorbed by the photoelectric conversion film 4. For this reason, in the radiation detector 20 pertaining to the present embodiment, the amount of radiation absorbed by the photoelectric conversion film 4 is small even in a case where the radiation passes through the TFT substrate 30 because of the irradiation side sampling type, so a drop in sensitivity with respect to the radiation can be suppressed. In the irradiation side sampling type, the radiation passes through the TFT substrate 30 and reaches the scintillator 8, but in a case where the photoelectric conversion film 4 of the TFT substrate 30 is configured by an organic photoelectric conversion material in this way, there is virtually no absorption of the radiation by the photoelectric conversion film 4 and attenuation of the radiation can be kept small, so configuring the photoelectric conversion film 4 with an organic photoelectric conversion material is suited to the irradiation side sampling type.

Further, the amorphous oxide configuring the active layers 17 of the thin-film transistors 10 and the organic photoelectric conversion material configuring the photoelectric conversion film 4 are both capable of being formed into films at a low temperature. For this reason, the substrate 1 can be formed by plastic resin, aramid, or bionanofibers in which there is little absorption of radiation. In the substrate 1 formed in this way, the amount of radiation absorbed is small, so a drop in sensitivity with respect to the radiation can be suppressed even in a case where the radiation passes through the TFT substrate 30 because of the irradiation side sampling type.

Further, according to the present embodiment, as shown in FIG. 8, the radiation detector 20 is adhered to the top panel 41B inside the casing 41 in such a way that the TFT substrate 30 is on the top panel 41B side, but in a case where the substrate 1 is formed by plastic resin, aramid, or bionanofibers whose rigidity is high, the rigidity of the radiation detector 20 itself is high, so the top panel 41B of the casing 41 can be formed thin. Further, in a case where the substrate 1 is formed by plastic resin, aramid, or bionanofibers whose rigidity is high, the radiation detector 20 itself has flexibility, so the radiation detector 20 does not easily break even in a case where shock has been applied to the imaging region 41A.

As described in detail above, in the present embodiment, plural radiation detection pixels (in the present embodiment, the radiation detection pixels 32A) with mutually different characteristics are arranged in a radiation detector (in the present embodiment, the radiation detector 20), and the radiation detection pixels are used selectively according to the characteristics to detect a state of application of radiation, so the state of application of the radiation can be detected more accurately compared to a case where the radiation detector does not have these pixels.

Further, in the present embodiment, the radiation detection pixels are arranged in different positions in the imaging region, so the state of application of the radiation can be detected more accurately as a result of being able to select and use, in accordance with the size and so forth of the part to be imaged, the pixels used for detecting the state of application of the radiation.

Further, in the present embodiment, the state of application of the radiation is the start of application of the radiation and the applied dose of the radiation, and the radiation detection pixels used in the detection of the state of application are selected in accordance with the state of application, so the state of application of the radiation can be detected more accurately as a result of being able to select and use, in accordance with the state of application, the pixels used to detect the state of application of the radiation.

Further, in the present embodiment, the characteristics are different because of the plural radiation detection pixels being connected to amplifiers (in the present embodiment, the variable gain pre-amps 92 and 92') that amplify, at mutually different gains, signals represented by the electric charges stored by the radiation detection pixels. Further, the characteristics are different because of the plural radiation detection pixels being connected to low-pass filters (in the present embodiment, the LPFs 96 and 96') that perform low-pass filtering at mutually different low-pass filtering frequencies with respect to signals represented by the electric charges stored by the radiation detection pixels. Moreover, the characteristics are different because of the plural radiation detection pixels being connected to synthesizing means (in the present embodiment, the binning components 94) that synthesize mutually different numbers of signals represented by the electric charges stored by the radiation detection pixels. Consequently, the characteristics can be realized easily.

Moreover, in the present embodiment, the radiation detector includes dedicated lines (in the present embodiment, the direct read-out lines 38) for reading out the stored electric charges from the radiation detection pixels, so the radiographic image can be captured at a higher speed as a result of being able to detect the state of application of the radiation can be detected independently of the action of capturing the radiographic image.

The present invention has been described above using an embodiment, but the technical scope of the present invention is not limited to the scope described in the embodiment. Various changes or improvements can be made to the embodiment without departing from the gist of the invention, and the technical scope of the present invention also includes embodiments to which such changes or improvements have been made.

Further, the embodiment is not intended to limit the inventions pertaining to the claims, and it is not the case that all combinations of features described in the embodiment are essential to the solution of the invention. The embodiment includes inventions of various stages, and various inventions can be extracted by appropriately combining the plural configural requirements disclosed. Even when several configural requirements are omitted from all the configural requirements disclosed in the embodiment, configurations from which those several configural requirements have been omitted can also be extracted as inventions as long as effects are obtained.

For example, in the above embodiment, a case was described where, as shown in FIG. 6, the radiation detection pixels 32A are arranged symmetrically with respect to both the up-and-down direction and the left-and-right direction in the central portion detection regions and the peripheral edge portion detection regions, but the present invention is not limited to this, and there are no particular limitations on the arranged positions of the radiation detection pixels 32A. However, by arranging the radiation detection pixels in such a way as to be symmetrical with respect to the up-and-down direction and the left-and-right direction like in the present embodiment, the electronic cassette 40 can be used without having to worry about the up-and-down direction of the electronic cassette 40, so user-friendliness can be improved, which is preferred.

Here, in a case where the radiation detection pixels 32A are arranged in such a way as to not be symmetrical with respect to the up-and-down direction, it is preferred that the electronic cassette 40 be given a configuration in which direction detecting means such as an acceleration sensor or a gyro is disposed in the electronic cassette 40 and in which the positions of the radiation detection pixels 32A are identified in accordance with the direction of the electronic cassette 40 identified by the direction detecting means.

In the above embodiment, some of the pixels 32 disposed in the radiation detector 20 are used as the radiation detection pixels 32A, so needless to say it is preferred that adjacent radiation detection pixels 32A be spaced apart from each other to an extent that the defective pixel correction can be implemented.

Further, in the above embodiment, the radiation detection pixels 32A whose characteristics are different are dispersed and arranged by group positions where the characteristics in the imaging region of the radiation detector 20 can be optimally utilized, so the electronic cassette 40 may also be given a configuration where marks such as characters, symbols, or designs denoting the corresponding characteristics are disposed in positions on the front surface of the top panel 41B of the electronic cassette 40 corresponding to the positions in which the pixel groups of the radiation detection pixels 32A are arranged, so that the radiographer may reference the marks and select and use the radiation detection pixels 32A. In this case, the electronic cassette 40 may be given a configuration in which the colors of the marks are changed per characteristic.

Figure 17:
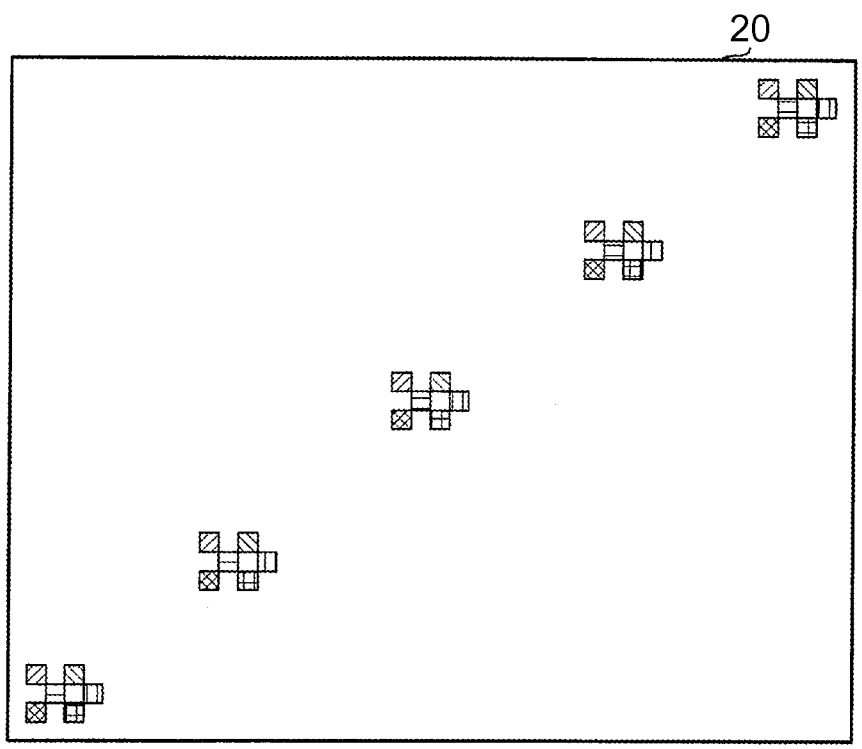
FIG. 17 is a plan view showing another example of an arrangement of the radiation detection pixels pertaining to the embodiment.

Further, in the above embodiment, as shown in FIG. 6 and FIG. 10, a case was described where the radiation detection pixels 32A are arranged in such a way as to have different characteristics per arrangement region, but the present invention is not limited to this; for example, as shown in FIG. 17, the radiation detector 20 may also be given a configuration in which the radiation detection pixels 32A that have different characteristics are arranged in the same arrangement regions.

Further, in the above embodiment, a case was described where some of the pixels 32A disposed in the radiation detector 20 are used as the radiation detection pixels 32A, but the present invention is not limited to this; for example, the radiation detector 20 may also be given a configuration in which the radiation detection pixels 32A are layered in the radiation detector 20 as a separate layer from the pixels 32. In this case, no defective pixels arise, so the quality of the radiographic image can be improved compared to the above embodiment. Further, in this case, it becomes possible to ensure that the radiation detection pixels have different characteristics depending on the light-receiving area, the constituent material, and so forth of the radiation detection pixels 32A, and it becomes unnecessary to dispose the second signal processing unit 55 pertaining to the above embodiment.

Further, in the above embodiment, a case was described where the radiation detection pixels 32A are dedicated pixels that detect the radiation, but the present invention is not limited to this and may also be given a configuration that uses the radiation detection pixels 32A doubly as the radiographic image acquisition pixels 32B.

Further, in the above embodiment, a case was described where just two types of gains of the variable gain pre-amps and two types of low-pass filtering frequencies of the LPFs were disposed, but the present invention is not limited to this and may also be given a configuration where three or more types of these are disposed. Further, the number of the electrical signals synthesized by the binning components is also not limited to two, and the present invention may also be given a configuration where the number is three or more.

Further, in the above embodiment, a case was described where the radiation detection pixels 32A were used to detect the start of application of the radiation and the applied dose, but the present invention is not limited to this and may also be given a configuration where the radiation detection pixels 32A are used to detect the stop of application of the radiation.

Further, the applied conditions of the gains of the variable gain pre-amps, the binning state resulting from the binning components, and the low-pass filtering frequencies of the LPFs described in the above embodiment are examples, and example configurations described below can also be employed.

Regarding the gains of the variable gain pre-amps, a configuration that applies a lower gain the greater the applied dose of the radiation X is, a configuration that applies a higher gain in the case of capturing a moving image than in the case of capturing a still image, and a configuration that applies a relatively high gain in the case of detecting the start of the application of the radiation and applies a relatively low gain in the case of detecting the end of the application of the radiation and the applied dose can be exemplified.

Further, regarding the binning states resulting from the binning components, a configuration that applies a lower binning number the greater the applied dose of the radiation X is, a configuration that applies a higher binning number in the case of capturing a moving image than in the case of capturing a still image, and a configuration that applies a relatively high binning number in the case of detecting the start of the application of the radiation and applies a relatively low binning number in the case of detecting the end of the application of the radiation and the applied dose can be exemplified.

Moreover, regarding the low-pass filtering frequencies of the LPFs, a configuration that applies a lower low-pass filtering frequency the lower the tube current and tube voltage when emitting the radiation X are and a configuration that applies a relatively low low-pass filtering frequency as the low-pass filtering frequency corresponding to the radiation detection pixels positioned in the imaging region where the part to be imaged is positioned can be exemplified.

Further, in the above embodiment, a case was described where the radiation detection pixels 32A arranged side-by-side in the row direction in the radiation detector 20 are connected to common direct read-out lines 38, but the present invention is not limited to this and may also be given a configuration where all the radiation detection pixels 32A are individually connected to different direct read-out lines 38.

Further, in the above embodiment, a case was described where the sensor portions 13 are configured to include the organic photoelectric conversion material in which electric charge is generated as a result of receiving the light generated by the scintillator 8, but the present invention is not limited to this and may also be given a configuration that applies sensor portions configured to not include the organic photoelectric conversion material as the sensor portions 13.

Further, in the above embodiment, a case was described where the radiation detector 20 and the case 42 accommodating the cassette controller 58 and the power source 70 are placed inside the casing 41 of the electronic cassette 40 in such a way as to not coincide, but the present invention is not limited to this. For example, the cassette controller 58 and the power source 70 may also be placed in such a way as to coincide with the radiation detector 20.

Further, in the above embodiment, a case was described where communication is performed wirelessly between the electronic cassette 40 and the console 110 and between the radiation generator 120 and the console 110, but the present invention is not limited to this and may also be given a configuration where, for example, communication between at least one of these is performed via wires.

Further, in the above embodiment, a case was described where X-rays are applied as the radiation, but the present invention is not limited to this and may also be given a configuration where another form of radiation such as gamma rays is applied.

In addition, the configuration of the RIS 100 (see FIG. 1), the configuration of the radiographic imaging room (see FIG. 2), the configuration of the electronic cassette 40 (see FIG. 3 to FIG. 8 and FIG. 10), and the configuration of the imaging system 104 (see FIG. 9) described in the above embodiment are examples, and needless to say unnecessary portions can be deleted therefrom, new portions can be added thereto, and states of connection and so forth can be changed without departing from the gist of the present invention.

Further, the configuration of the initial information described in the above embodiment is also an example, and needless to say unnecessary information can be deleted therefrom and new information can be added thereto without departing from the gist of the present invention.

Further, the flows of processing by the various programs (see FIG. 11 and FIG. 13 to FIG. 15) described in the above embodiment are also examples, and unnecessary steps can be deleted therefrom, new steps can be added thereto, and the processing order can be switched around without departing from the gist of the present invention.

Further, the configuration of the initial information input screen (see FIG. 12) described in the above embodiment is also an example, and unnecessary information can be deleted therefrom and new information can be added thereto without departing from the gist of the present invention.

What is claimed is:

1. A radiographic imaging device comprising:
a radiation detector comprising a plurality of radiographic image acquisition pixels for capturing a radiographic image that are arranged in a matrix in an imaging region, and that acquire image information representing the radiographic image by converting applied radiation into electric charges and storing the electric charges, and a plurality of radiation detection pixels that are arranged in an imaging region as a separate layer from the plurality of radiographic image acquisition pixels, and that detect the applied radiation by converting the applied radiation into electric charges and storing the electric charges, at least one subset of the plurality of radiation detection pixels having different characteristics from the remaining radiation detection pixels that are not included in the subset, wherein the subset comprises fewer than all the pixels within the plurality of radiation detection pixels; and
a detecting unit that uses the radiation detection pixels selectively according to the different characteristics to detect a state of application of the radiation.

2. The radiographic imaging device according to claim 1, further comprising an acquiring unit that acquires an imaging condition for capturing the radiographic image, wherein the detecting unit uses the radiation detection pixels which have characteristics corresponding to the imaging condition acquired by the acquiring unit to detect the state of application of the radiation.

3. The radiographic imaging device according to claim 1, wherein the radiation detection pixels are arranged in different positions in the imaging region.

4. The radiographic imaging device according to claim 1, wherein
the state of application of the radiation is at least one of a start of application of the radiation, an end of application of the radiation, or an the applied dose of the radiation, and
the detecting unit selects the radiation detection pixels used in the detection of the state of application in accordance with the state of application of the radiation to be detected.

5. The radiographic imaging device according to claim 1, wherein the subset of radiation detection pixels have different characteristics due to being connected to amplifiers that amplify, at different gains, signals represented by the electric charges stored by the subset of radiation detection pixels.

6. The radiographic imaging device according to claim 5, wherein the subset of radiation detection pixels have different characteristics due to being connected to low-pass filters that perform low-pass filtering at different low-pass filtering frequencies with respect to signals represented by the electric charges stored by the subset of radiation detection pixels.

7. The radiographic imaging device according to claim 5, wherein the subset of radiation detection pixels have different characteristics due to being connected to a synthesizing unit that synthesize different numbers of signals represented by the subset of radiation detection pixels.

8. The radiographic imaging device according to claim 1, wherein the subset of radiation detection pixels have different characteristics due to being connected to low-pass filters that perform low-pass filtering at different low-pass filtering frequencies with respect to signals represented by the electric charges stored by the subset of radiation detection pixels.

9. The radiographic imaging device according to claim 1, wherein the subset of radiation detection pixels have different characteristics due to being connected to a synthesizing unit that synthesize different numbers of signals represented by the subset of radiation detection pixels.

10. The radiographic imaging device according to claim 1, wherein
the subset of radiation detection pixels have different characteristics due to being connected to amplifiers that amplify, at different gains, signals represented by the electric charges stored by the subset of radiation detection pixels,
the subset of radiation detection pixels have different characteristics due to being connected to low-pass filters that perform low-pass filtering at different low-pass filtering frequencies with respect to signals represented by the electric charges stored by the subset of radiation detection pixels, and
the subset of radiation detection pixels have different characteristics due to being connected to a synthesizing unit that synthesize different numbers of signals represented by the subset of radiation detection pixels.

11. The radiographic imaging device according to claim 1, wherein the imaging condition is at least one of a part to be imaged, a region in which the part to be imaged is placed when capturing the radiographic image, whether the imaging is imaging to capture a moving image or a still image, or an applied dose of the radiation.

12. The radiographic imaging device according to claim 1, wherein the radiation detector further comprises dedicated lines for reading out the stored electric charges from the radiation detection pixels.

13. A non-transitory computer readable medium storing a program executed by a radiographic imaging device comprising a radiation detector comprising a plurality of image acquisition pixels for capturing a radiographic image that are arranged in a matrix in an imaging region, and that acquire image information representing the radiographic image by converting applied radiation into electric charges and storing the electric charges, and a plurality of radiation detection pixels that are arranged in an imaging region as a separate layer from the plurality of radiographic image acquisition pixels, and that detect the applied radiation by converting the applied radiation into electric charges and storing the electric charges, at least one subset of the plurality of radiation detection pixels having different characteristics from the remaining radiation detection pixels that are not included in the subset, wherein the subset comprises fewer than all the pixels within the plurality of radiation detection pixels, and, the program causing a computer to function as
an acquiring unit that acquires an imaging condition for capturing the radiographic image and a detecting unit that uses the radiation detection pixels having characteristics corresponding to the imaging condition acquired by the acquiring unit to detect a state of application of the radiation.

* * * * *